US009193729B2

(12) United States Patent
Metcalf, III et al.

(10) Patent No.: US 9,193,729 B2
(45) Date of Patent: Nov. 24, 2015

(54) INHIBITING TRANSIENT RECEPTOR POTENTIAL ION CHANNEL TRPA1

(71) Applicant: Cubist Pharmaceuticals, Inc., Lexington, MA (US)

(72) Inventors: Chester A. Metcalf, III, Needham, MA (US); Yu Gui Gu, Acton, MA (US); Spencer D. Kimball, East Windsor, NJ (US); Qingy Li, Waltham, MA (US); Blaise S. Lippa, Acton, MA (US); Dominic Ryan, Littleton, MA (US); Xinyuan Wu, Newton, MA (US); Dong Zou, Concord, MA (US)

(73) Assignee: Cubist Pharmaceuticals, Inc., Lexington, MA (US)

( * ) Notice: Subject to any disclaimer, the term of this patent is extended or adjusted under 35 U.S.C. 154(b) by 0 days.

(21) Appl. No.: 13/832,240

(22) Filed: Mar. 15, 2013

(65) Prior Publication Data

US 2013/0274273 A1 Oct. 17, 2013

Related U.S. Application Data

(63) Continuation of application No. 13/571,288, filed on Aug. 9, 2012, now abandoned.

(60) Provisional application No. 61/521,705, filed on Aug. 9, 2011.

(51) Int. Cl.
*A01N 43/54* (2006.01)
*A01N 43/90* (2006.01)
*A01N 43/58* (2006.01)
*A61K 31/519* (2006.01)
*A61K 31/4188* (2006.01)
*C07D 473/08* (2006.01)

(52) U.S. Cl.
CPC .................................. *C07D 473/08* (2013.01)

(58) Field of Classification Search
CPC .................. A61K 31/519; A61K 31/4188
See application file for complete search history.

(56) References Cited

U.S. PATENT DOCUMENTS

| | | |
|---|---|---|
| 7,582,658 B2 | 9/2009 | Miyoshi et al. |
| 7,671,061 B2 | 3/2010 | Moran et al. |
| 8,163,761 B2 | 4/2012 | Ng et al. |
| 2007/0219222 A1 | 9/2007 | Moran et al. |
| 2010/0249154 A1 | 9/2010 | Ng et al. |
| 2011/0151018 A1 | 6/2011 | Garrity et al. |
| 2012/0083474 A1 | 4/2012 | Berthelot et al. |
| 2012/0157411 A1 | 6/2012 | Kumar et al. |
| 2012/0316136 A1 | 12/2012 | Khairatkar-Joshi et al. |
| 2014/0158116 A1 | 6/2014 | Chong et al. |
| 2014/0163048 A1 | 6/2014 | Barker et al. |
| 2014/0206650 A1 | 7/2014 | Lippa et al. |

FOREIGN PATENT DOCUMENTS

| | | |
|---|---|---|
| RU | 2352338 C2 | 4/2009 |
| WO | WO-2005/059107 A2 | 6/2005 |
| WO | WO2007/002933 A1 | 12/2008 |
| WO | WO-2009/002933 A1 | 12/2008 |
| WO | WO2009144548 A1 | 12/2009 |
| WO | WO2010004390 A1 | 1/2010 |
| WO | WO2010/138879 A1 | 2/2010 |
| WO | WO2010/075353 A1 | 7/2010 |
| WO | WO2010109287 A1 | 9/2010 |
| WO | WO2010141805 A1 | 12/2010 |
| WO | WO2011043954 A1 | 4/2011 |
| WO | WO2011114184 A1 | 9/2011 |
| WO | WO2012050512 A1 | 4/2012 |
| WO | WO2013/023102 A1 | 2/2013 |
| WO | WO-2014/026073 A1 | 2/2014 |
| WO | WO-2014/113671 A1 | 7/2014 |

OTHER PUBLICATIONS

Heppelmann, et al: Inhibitory effect of amiloride and gadolinium on fine afferent nerves in the rat knee: evidence of mechanogated ion channels in joints; Experimental Brain Research, 2005, vol. 167, No. 1, pp. 114-118.
Klement, et al: Characterization of a Ligand Binding Site in the Human Transient Receptor Potential Ankyrin 1 Pore; Biophysical Journal, vol. 104, Feb. 2013, pp. 798-806.
Lu, et al., TRPA1b, a functional human vanilloid receptor splice variant; Mol. Pharmacol., Apr. 2005; 67(4); pp. 1119-1127.
Mills, et al: SAR mining and its application to the design of TRPA1 antagonists, MedChemComm; Downloaded on Nov. 23, 2011; Published on Oct. 19, 2011 on http://pubs.rsc.org | doi:10.1039/C1MD00213A.
Nagata, et al: Nociceptor and Hair Cell Transducer Properties of TRPA1, a Channel for Pain and Hearing; The Journal of Neuroscience, 2005, vol. 25, No. 16, pp. 4052-4062.
Pfizer, Prospective use: TrpA1. 42nd National Organic Chemistry Symposium, Princeton, NJ, Jun. 5-9, 2011, Poster.
Andersson, et al: TRPA1 mediates spinal antinociception induced by acetaminophen and the cannabinoid Δ9-tetrahydrocannabiorcol; Nature Communications, 2:551, (2011), 11 pages.
Banke, The dilated TRPA1 channel pore state is blocked by amilorideand analogues; Brain Research, 1381, pp. 21-30 (2011).
Banner, et al: TRP channels: Emerging targets for respiratory disease; Pharmacology & Therapeutics; vol. 130, pp. 371-384 (2011).
Baraldi, et al: Transient Receptor Potential Ankyrin 1 (TRPA1) Channel as Emerging Target for Novel Analgesics and Anti-Inflammatory Agents; J.Med.Chem, 53, pp. 5085-5107 (2010).
Brouwers, et al: In vitro behavior of a phosphate ester prodrug of amprenavirin human intestinal fluids and in the Caco-2 system: Illustration of intraluminal supersaturation; International Journal of Pharmaceutics, vol. 336, pp. 302-309 (2007).
Caceres: A sensory neuronal ion channel essential for airway inflammation and hyperactivity in asthma; PNAS vol. 106, No. 22, pp. 9909-9104 (Jun. 2, 2009).

(Continued)

*Primary Examiner* — Svetlana M Ivanova
(74) *Attorney, Agent, or Firm* — Choate, Hall & Stewart, LLP; Fangli Chen; John P. Rearick

(57) ABSTRACT

This disclosure describes a novel compounds and pharmaceutical compositions for inhibiting the TRPA1 ion channel and/or medical conditions related to TRPA1, such as pain.

11 Claims, 9 Drawing Sheets

(56) References Cited

OTHER PUBLICATIONS

Cao, De-Shou, et al: Expression of Transient Receptor Potential Ankyrin 1 (TRPA1) and Its Role in Insulin Release from Rat Pancreatic Beta Cells; Plos One, vol. 7, Issue 5 (2012), 10 pages.

Chen, Jun, et al: Selective blockade of TRPA1 channel attenuates pathological pain without altering noxious cold sensation or body temperature regulation; Pain, vol. 152, pp. 1165-1172 (2011).

del Camino, Donato, et. al: TRPA1 Contributes to Cold Hypersensitivity; Journal of Neuroscience, 30(45), pp. 15165-15174 (Nov. 10, 2010).

Facchinetti, Fabrizio, et al: The Rising Role of TRPA1 in Asthma; The Open Drug Discovery Journal, 2, pp. 71-80 (2010).

Fanger, Christopher, M., et. al: TRPA1 as an Analgesic Target; The Open Drug Discovery Journal, 2, pp. 64-70 (2010).

Fechner, Jorg, et al: Pharmacokinetics and Clinical Pharmacodynamics of the new Propofol Prodrug GPI 15715 in Volunteers; Anesthesiology, vol. 99, No. 2, 303-313 (Aug. 2003).

Fernandes, ES, et al: The functions of TRPA1 and TRPV1: moving away from sensory nerves; British Journal of Pharmacology, 166, 510-521 (2012).

Fischer, James, H., et al: Fosphenytoin Clinical Pharmacokinetics and Comparative Advantages in the Acute Treatment of Seizures; Clin Pharmacokinet, 42(1), 33-58 (2003).

Gijsen, Harrie, J.M. et al: Tricyclic 3,4-dihydropyrimidine-2-thione derivatives as potent TRPA1 antagonists; Bioorganic & Medicinal Chemistry Letters, 22, 797-800 (2012).

Gijsen, Harrie, J.M. et al: Tricyclic 3,4-dihydropyrimidine-2-thione derivatives as potent TRPA1 antagonists; Johnson & Johnson, Poster (2012).

International Search Report, PCT/US2012/050210, dated Sep. 11, 2012, 6 pages.

Indian Patent Application 2512-MUM-2008 date stamped Nov. 27, 2009, entitled "Uracil and 6-Azauracil Derivatives as TRPA1 Modulators," 41 pages.

Usmani, Omar, et al: Theobromine inhibits sensory nerve activation and cough; FASEB Journal (2004), 16 pages.

Koivisto, Ari, et al: Inhibiting TRPA1 ion channel reduces loss of cutaneous nerve fiber function in diabetic animals: Sustained activation of the TRPA1 channel contributes to thepathogenesis of peripheral diabetic neuropathy; Pharmacological Research (2011), 10 pages.

Krise, Jeffrey, P., et al: Prodrugs of phosphates, phosphonates, and phosphinates; Advanced Drug Delivery Reviews, 19, pp. 287-310 (1996).

Krise, Jeffrey, P., et al: Novel Prodrug Approach for Tertiary Amines: Synthesis and Preliminary Evaluation of N-Phosphonooxymethyl Prodrugs; J. Med. Chem., vol. 42, pp. 3094-3100 (1999).

Li, Weixing, et al: Identification of GS 4104 as an Orally Bioavailable Prodrug of the Influenza Virus Neuraminidase Inhibitor GS 4071; Antimicrobial Agents and Chemotherapy, vol. 42, No. 3., pp. 647-653 (Mar. 1998).

Yagi, Shigenori, et al: Development of Anti-Influenza Virus Drugs I: Improvement of Oral Absorption and in Vivo Anti-Influenza Activity of Stachyflin and Its Derivatives; Pharmaceutical Research, vol. 16, No. 7, pp. 1041-1046, (1999).

McNamara, Colleen, R., et al: TRPA1 mediates formalin-induced pain; PNAS vol. 104, No. 33, pp. 13525-13530, Aug. 14, 2007.

Mills, James, E.J., et al: SAR mining and its application to the design of TRPA1 antagonists; MedChemComm, (2011); D01:10.1039/c1md00213a; 5 pages.

Moran, Magdalene, M., et al: Transient Receptor Potential Ankyrin 1 as a Target for Perioperative Pain Management; Anesthesiology, vol. 117, pp. 8-9 (2012).

Moran, Magdalene, et. al: Transient receptor potential channels as therapeutic targets; Nature Reviews, vol. 10, pp. 601-620 (Aug. 2011).

Wei, Hong, et al: Transient Receptor Potential Ankyrin 1 Ion Channel Contributes to Guarding Pain and Mechanical Hypersensitivity in a Rat Model of Postoperative Pain; Anesthesiology, vol. 117, pp. 137-148 (2012).

Vallin, K.S.A., et al: N-1-alkyl-2-oxo-2-aryl amides as novel antagonists of the TRPA1 receptor; Bioorganic & Medicinal Chemistry Letters, (2012) Manuscript, 8 pages.

Pochopin, Nancy, et al: Pharmocokinetics of Dapsone and Amino Acid Prodrugs of Dapsone; Drug Metabolism and Disposition, vol. 2 (5), pp. 770-775 (1994).

Pochopin, Nancy, et al: Amino acid derivatives of dapsone as water-soluble prodrugs; Intl Journal of Pharmaceutics, vol. 121, pp. 157-167 (1995).

Press Release Aug. 30, 2010, "Glenmark announces the Discovery of a novel chemical entity GRC 17536, a potential first-in-class molecule globally", Glenmark Pharmaceuticals Ltd., 2 pages.

Rech, Jason, et al: Recent advances in the biology and medicinal chemistry of TRPA1; Future Science, vol. 2(5), pp. 843-858 (2010).

Reilly, Regina: TRPA1 as a Pain Target: Challenges and Progress; Abbott, Cambridge Healthtech Institute International, (2009), 21 pages.

Ryckmans, Thomas, et al: Design and pharmacological evaluation of PF-4840154, a non-electrophilic reference agonist of the TrpA1 channel; Bioorganic & Medicinal Chemistry Letters, vol. 21, pp. 4857-4859 (2011).

Stella: A case for prodrugs: Fosphenytoin; Advanced Drug Delivery Reviews, vol. 19, pp. 311-330 (1996).

Stella, et al:Aqueous Solubility and Dissolution Rate Does Not Adequately Predict in Vivo Performance: A Probe Utilizing Some N-Acyloxymethyl Phenytoin Prodrugs, J. of Pharmaceutical Sciences, vol. 88, No. 8, Aug. 1999, 5 pages.

Stella, Valentino, J., et al: Prodrug strategies to overcome poor water solubility, Advanced Drug Delivery Reviews, 59, 677-694 (2007).

Stella, Valentino, J., et al: Site-specific drug delivery via prodrgus; Design of Prodrugs, pp. 177-198 (1985).

Bessac, et al: Breathtaking TRP Channels: TRPA1 and TRPV1 in Airway Chemosensation and Reflex Control; Physiology; 2008, vol. 23, pp. 360-370.

Nassini, et al: Transient Receptor Potential Ankyrin 1 Channel Localized to Non-Neuronal Airway Cells Promotes Non-Neurogenic Inflammation; PLoS One; Aug. 2012, vol. 7, Issue 8, e42454; 12 pages.

Nassenstein, et al: Expression and function of the ion channel TRPA1 in vagal afferent nerves innervating mouse lungs; J Physiology; 2008; vol. 586; pp. 1595-1604.

Panke, et al: A cell-based impedance assay for monitoring transient receptor potential (TRP) ion channel activity; Biosensors and Bioelectronics; 2011, vol. 26, pp. 2376-2382.

Santosh, et al: The Cells and Circuitry for Itch Responses in Mice; Science; 2013, vol. 340, pp. 968-971.

Wilson, et al: The Ion Channel TRPA1 Is Required for Chronic Itch; J. Neuroscience; 2013, vol. 33:22, pp. 9283-9294.

Roberson, et al: Activity-dependent silencing reveals functionally distinct itch-generating sensory neurons; Nature Neuroscience; 2013; vol. 16, pp. 910-918.

Banker, M.J. et al., Development and Validation of a 96-WII Equilibrium Dialysis Apparatus for Measuring Plasma Protein Binding, Journal of Pharmaceutical Sciences, 92(5): 967-74 (2003).

Bautista, D.M. et al., TRPA1 Mediates the Inflammatory Actions of Environmental Irritants and Proalgesic Agents, Cell, 124 (6):1269-1282 (2006).

Brennan, T.J. et al., Characterization of a rat model of incisional pain, Pain, 64(3): 493-501 (1996).

Dubuisson, D. and Dennis, S.G. et al., The Formalin Test: A quantitative study of the analgesic effects of morphine, meperidine, and brain stem stimulation in rats and cats, Pain, 4(2): 161-74 (1977).

Jordt, S.E. et al., Mustard oils and cannabinoids excite sensory nerve fibres through the TRP channel ANKTM1, Nature, 427(6971): 260-265 (2004).

Katsura, H. et al., Antisense knock down of TRPA1, but not TRPM8, alleviates cold hyperalgesia after spinal nerve ligation in rats, Exploratory Neurology, 200: 112-123 (2006).

Kremeyer, B. et al., A gain-of-function mutation in TRPA1 causes familial episodic pain syndrome, Neuron, 66(5):671-680 (2010).

Kwan, K.Y. et al., TRPA1 Contributes to Cold, Mechanical, and Chemical Nociception but Is Not Essential for Hair-Cell Transduction, Neuron, 50: 277-289 (2006).

(56) References Cited

OTHER PUBLICATIONS

Morozowich, W. and Karnes, H.A., Clindamycin 2-Phosphate, A Prodrug of Clindamycin, Prodrugs: Challenges and Rewards: Part 1, Biotechnology: Pharmaceutical Aspects, 5: 509-519 (2007).

Obata, K. et al., TRPA1 induced in sensory neurons contributes to cold hyperalgesia after inflammation and nerve injury, Journal of Clinical Investigation, 115(9): 2393-2401 (2005).

Abbott, F.V. et al., The formalin test: scoring properties of the first and second phases of the pain response in rats, Pain, 60(1):91-102 (1995).

Abraham, W.M., Animal models of asthma, Asthma and Rhinitis, Edited by Busse, W.W. and Holgate, S.T., Oxford: Blackwell Science, Chapter 78: 1205-1227 (2000).

Albuterol Inhalation, Drugs.com, 2012 <http://www.drugs.com/albuterol.html>.

Ibuprofen, Drugs.com, 2011 <http://www.drugs.com/ibuprofen.html>.

International Search Report for PCT/US2013/054246, 3 pages (Dec. 26, 2013).

International Search Report for PCT/US2014/012049, 4 pages (May 9, 2014).

Kerns, E.H., High throughput physicochemical profiling for drug discovery, Journal of Pharmaceutical Sciences, 90(11): 1838-1858 (2001).

Materazzi, S., TRPA1 and TRPV4 mediate paclitaxel-induced peripheral neuropathy in mice via a glutathione-sensitive mechanism, Pflugers Arch., European Journal of Physiology, 463(4):561-569 (2012).

Wermuth, C., Molecular Variations Based on Isoteric Replacements, The Practice of Medicinal Chemistry, Academic Press, 203-237 (1996).

Written Opinion for PCT/US2012/050210, 7 pages (Feb. 9, 2014).
Written Opinion for PCT/US2013/054246, 7 pages (Dec. 26, 2013).

INHIBITING TRANSIENT RECEPTOR POTENTIAL ION CHANNEL TRPA1

PRIORITY

This patent application is a continuation of U.S. patent application Ser. No. 13/571,288, filed Aug. 9, 2012, which claims priority to U.S. provisional patent application Ser. No. 61/521,705, filed Aug. 9, 2011. The contents of these applications are incorporated herein by reference in their entireties.

TECHNICAL FIELD

The present disclosure relates to compounds and methods for treating pain, for example by inhibiting the Transient Receptor Potential A1 ion channel (TRPA1).

BACKGROUND

TRPA1 is a non-selective cation channel related to pain sensation in humans. TRPA1 is found in sensory neurons and functions as a signal transduction receptor linking inflammation to pain. Activation of TRPA1 can cause pain by inducing firing of nociceptive neurons and driving central sensitization in the spinal cord. TRPA1 stimulation can also increase firing of sensory neurons, leading to the release of pro-inflammatory neuropeptides such as NK-A, substance P and CGRP (which induce vasodilation and help recruit immune cells). A variety of endogenous reactive compounds produced during inflammation activate TRPA1 (including 4-hydroxynonenal released during liposome peroxidation; cyclopentane prostaglandins synthesized by COX enzymes; hydrogen peroxide produced by oxidative stress). TRPA1 can also be activated by a variety of stimuli, including natural products (e.g., allyl isothiocyanate, or AITC), environmental irritants (e.g., acrolein), amphipathic molecules (e.g., trinitrophenol and chlorpromazine) and pharmacological agents. Activation of TRPA1 also sensitizes TRPA1 to cold. Furthermore, a gain-of-function mutation in TRPA1 causes familial episodic pain syndrome; patients suffering from this condition have episodic pain that may be triggered by cold. (Kremeyer et al., Neuron. 2010 Jun. 10; 66(5):671-80). Thus, TRPA1 is believed to play a role in pain, including pain related to nerve damage, cold allodynia and inflammatory pain.

TRPA1 inhibitor compounds can be used to treat pain. Compounds that inhibit the TRPA1 ion channel can be useful, for example, in treating conditions ameliorated, eliminated or prevented by inhibition of the TRPA1 ion channel (e.g., medical conditions causing pain). Inhibition of TRPA1 (e.g., by genetic ablation and chemical antagonism) has been shown to result in reduced pain behavior in mice and rats. Knockout mice lacking functional TRPA1 have diminished nociceptive responses to TRPA1 activators (including AITC, formalin, acrolein, 4-hydroxynonenal) and, in addition, have greatly reduced thermal and mechanical hypersensitivity in response to the inflammatory mediator bradykinin (e.g., Kwan, K. Y. et al. Neuron 2006, 50, 277-289; Bautista, D. M. et al. Cell 2006, 124, 1269-1282). In animal pain models, down regulation of TRPA1 expression by gene specific antisense oligonucleotides prevented and reversed cold hyperalgesia induced by inflammation and nerve injury (See, e.g., Obata, K. et al., Journal of Clinical Investigation 2005, 115, 2393-2401; Jordt, S. E. et al., Nature 2004, 427, 260-265; Katsura, H. et al., Exploratory Neurology 2006, 200, 112-123). TRPA1 inhibitor compounds are also effective in a variety of rodent pain models. TRPA1 inhibitors have been shown to reduce mechanical hypersensitivity and cold allodynia following inflammation induced by Complete Freund's Adjuvant (without altering normal cold sensation in naïve animals) and also to improve function in the rat mono-iodoacetate osteoarthritis model. (See, del Camino, D. et al. (2010). TRPA1 contributes to cold hypersensitivity. *J Neurosci* 30, 15165-15174; and Chen, J. et al., (2011). Selective blockade of TRPA1 channel attenuates pathological pain without altering noxious cold sensation or body temperature regulation. *Pain* 152, 1165-72.) TRPA1 inhibitor compounds have demonstrated reduced pain behavior in rodents injected with AITC (mustard oil), formalin, cinnamaldehyde, acrolein and other TRPA1 activators. (See, Jordt, S. E. et al., Nature 2004, 427, 260-265; Chen, J. et al., (2011). Selective blockade of TRPA1 channel attenuates pathological pain without altering noxious cold sensation or body temperature regulation. *Pain* 152, 1165-72.)

Recently, a TRPA1 inhibiting compound was disclosed as compound 1 in PCT patent application PCT/US2009/069146 (published as WO2010/075353A1 on Jul. 1, 2010):

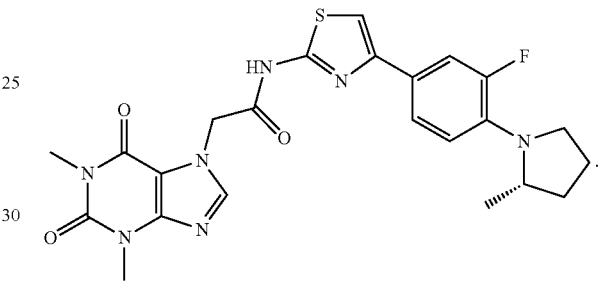

However, there remains a need to identify compounds that safely modulate (e.g., inhibit) ion channels involved in pain, including a need for pharmaceutical compositions that inhibit the TRPA1 ion channel. In particular, there is a need to identify compounds that inhibit TRPA1 without serum biomarkers of hepatotoxicity. Such compounds are useful, for example, both as research tools and as therapeutic agents (e.g., for the treatment of pain).

SUMMARY

The compound of Formula (I) is a novel antagonist of the human and animal TRPA1 channel.

Formula (I)

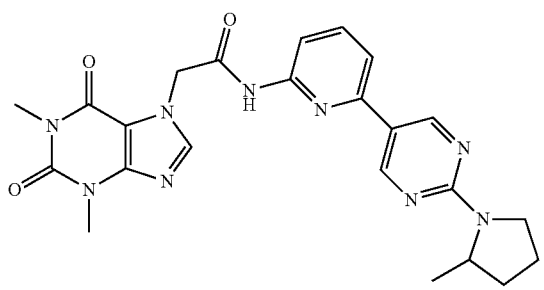

The compound of Formula (Ia) is a first stereoisomer of Formula (I) that can be synthesized according to the synthesis of FIG. 1A, as described in Example 1, and as a pharmaceutically acceptable salt (e.g., a hydrochloride salt described in Example 2).

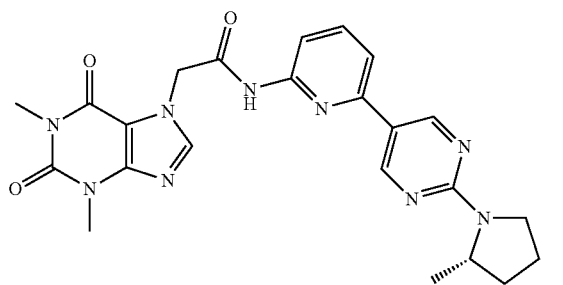

Formula (Ia)

The compound of Formula (Ia) is a novel small molecule antagonist of the human TRPA1 channel in both in vitro and in vivo testing. The compound of Formula (Ia) is also a highly selective in vitro inhibitor of TRPA1. For example, the compound of Formula (Ia) blocks inward currents through TRPA1 in rat, dog and human TRPA1 (Example 3). The antagonist effect of the compound of Formula (IIa) against human TRPA1 (hTRPA1) was measured in a whole cell patch configuration (Example 3). Furthermore, the compound of Formula (Ia) is highly selective for TRPA1 as compared with known TRP channels and voltage-gated ion channels (Example 3). The compound of Formula (Ia) can be used in assays for identifying compounds that inhibit TRPA1. A compound of Formula (I) can also be used in a method of modulating a TRPA1 ion channel, comprising contacting a cell with a compound having the structure of Formula I (e.g, a compound of Formula (Ia)), or a pharmaceutically acceptable salt thereof.

The compound of Formula (Ia) is an active pharmaceutical compound in multiple in vivo rat models of pain, including pain induced by direct activation of the TRPA1 channel with formalin injection (Example 5), cold allodynia following chronic Complete Freund's Adjuvant-induced inflammation (Example 6), and a rodent surgical model involving the incision of the plantar surface of the hind paw (Example 7).

The compound of Formula (Ib) is a second stereoisomer of Formula (I) that can be synthesized according Example 1c, and as a pharmaceutically acceptable salt.

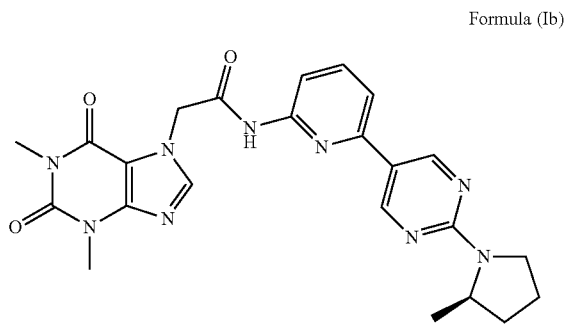 [SMILES: C[C@@H]1CCCN1c1ncc(-c2cccc(NC(=O)Cn3cnc4c3c(=O)n(C)c(=O)n4C)n2)cn1]

Formula (Ib)

The compound of Formula (Ib) is a second stereoisomer of Formula (I), and is a novel small molecule antagonist of the human TRPA1 channel in in vitro testing. Pharmaceutical compositions comprising a compound of Formula (I) (e.g., a compound of Formula (Ia)) are useful for administration for the treatment of pain. Other pharmaceutical compositions can include a compound of Formula (I) containing compounds of Formula (Ia) and/or Formula (Ib). The pharmaceutical compositions comprising the compound(s) of Formula (I) (e.g., compounds of Formula (Ia) and/or Formula (Ib)) are useful in the manufacturing of pharmaceutical compositions for treating pain.

A compound of Formula (I) (e.g., Formula (Ia) and/or Formula (Ib)) is also useful in the manufacturing of pharmaceutical compositions for treating a respiratory condition, preferably a condition responsive to a TRPA1 inhibitor.

Pharmaceutical compositions comprising the compound of Formula (I) (e.g., Formula (Ia)), and pharmaceutically acceptable salts and formulations thereof (e.g., pharmaceutical compositions including the compound of Formula (I) (e.g., Formula (Ia)) combined with a cyclodextrin), for instance hydroxypropyl-beta-cyclodextrin or the sulfobutylether β-cyclodextrin compound available under the tradename Captisol®) are useful in the treatment of pain, including inflammatory and post-operative pain. In addition, pharmaceutical compositions comprising the compound of Formula (I), (e.g., Formula (Ia)) can include a pharmaceutically acceptable salt of Formula (I) (e.g., Formula (Ia)) in formulations thereof that do not contain a cyclodextrin.

The compounds of Formula (I) (e.g., Formula (Ia)) and pharmaceutically acceptable salts thereof are also useful as research tools, for example in assays including the modulation of the TRPA1 ion channel.

BRIEF DESCRIPTION OF THE DRAWINGS

FIG. 2 shows the measured pain duration (as the number (n) of seconds over a 2 minute observation period) in a rodent formalin injection pain model for various pharmaceutical compositions containing different amounts of the compound of Formula (Ia), a vehicle delivered intraperitoneally (i.p.), and the comparator compound of Formula (II).

FIG. 3 shows the change in PWL score as a function of the concentration of the compound of Formula (Ia), as well as the PWL scores observed upon administration of the vehicle alone and a comparator pharmaceutical composition containing the comparator compound of Formula (II).

FIG. 4 shows the change in guarding score as a function of the administered concentration of the compound of Formula (Ia), as well as the guarding scores observed upon administration of the vehicle alone and comparator pharmaceutical compositions containing the comparator compound of Formula (III) or ketoprofen.

DETAILED DESCRIPTION

A compound of Formula (I) (e.g., Formula (Ia)) and pharmaceutically acceptable salts thereof, are useful for the inhibition of the TRPA1 ion channel in pharmaceutical compositions as well as research tools.

Formula (I)

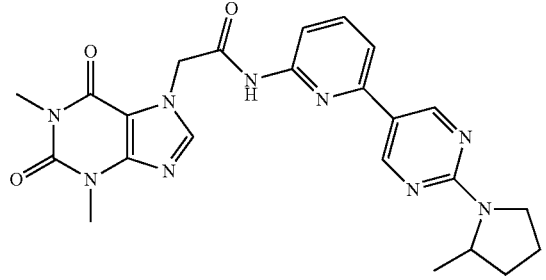

Synthesis of the Compound of Formula (I) and Salts Thereof

Figure 1A:
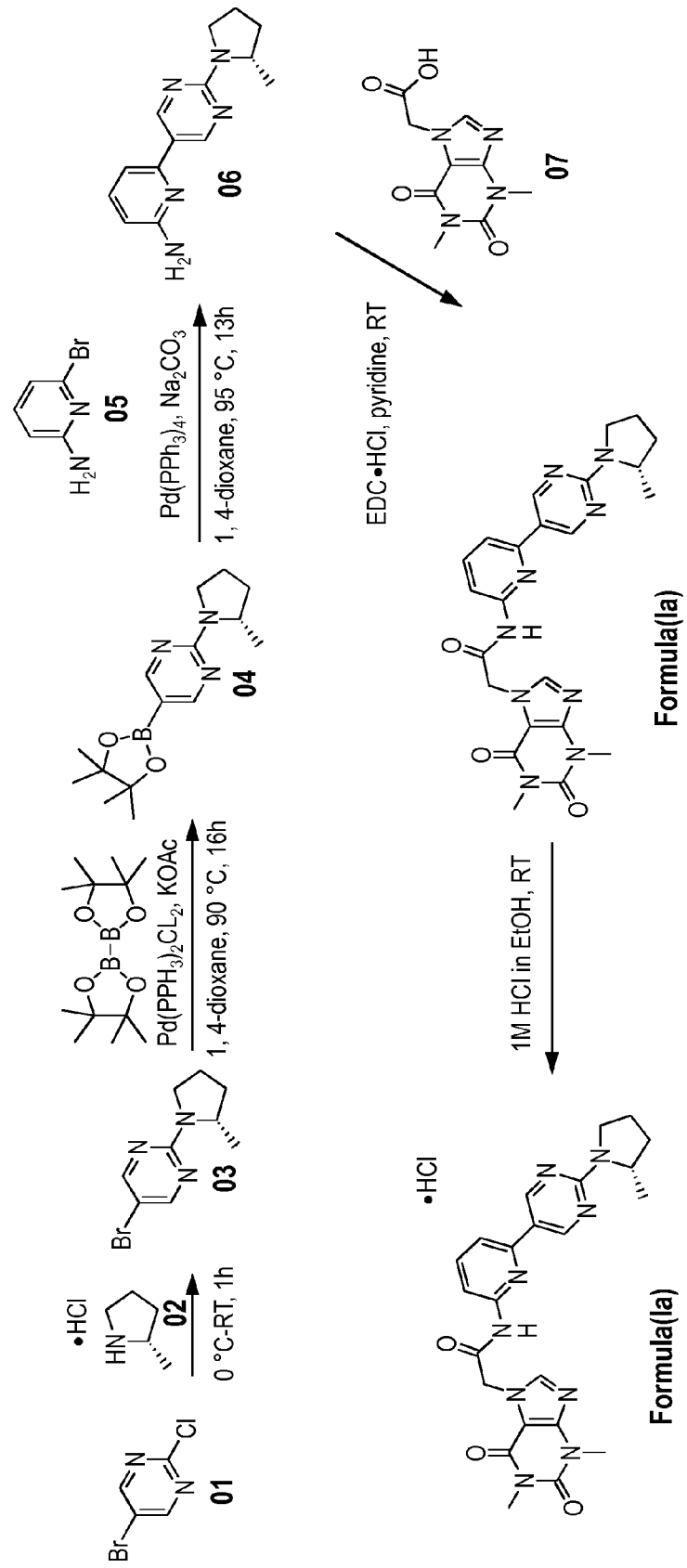
FIG. 1A is an exemplary reaction scheme to synthesize a compound of Formula (Ia), as described in Example 1A.

The compound of Formula (Ia) is a stereoisomer of Formula (I) that can be made by multi-step synthetic processes shown in FIG. 1A, as described in Example 1A.

Formula (Ia)

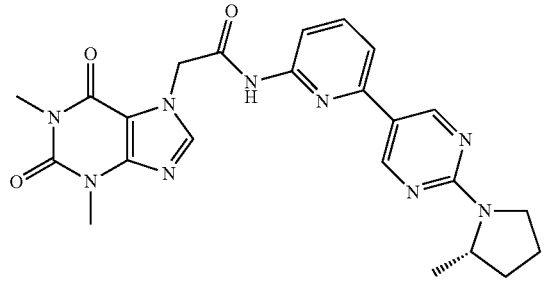

Briefly, referring to FIG. 1A, the compound of Formula (Ia) can be formed by: (1) reacting (S)-2-methylpyrrolidine $O_2$ with 5-bromo-2-chloropyrimidine 01 to form the intermediate compound 03, (2) coupling the compound 03 intermediate with compound 05 (6-bromo-2-aminopyridine) by one or more reactions to form the intermediate compound 06, and (3) reacting compound 06 with compound 07 in a coupling reaction to form the compound of Formula (Ia). While coupling of the compound 03 intermediate with compound 05 can be performed via the intermediate compound 04, as shown in FIG. 1A and described in Example 1A, other synthetic schemes are also suitable for preparation of the compound of Formula (Ia). As described in Example 1A and FIG. 1A, the intermediate compound 06 can be formed by reacting compound 03 with bis(pinacolato)diboron and other materials to form the intermediate compound 04, followed by reaction of the intermediate compound 04 with 6-bromo-2-aminopyridine (compound 05) to obtain the intermediate compound 06. Each of the reaction steps can be performed with suitable reagents with reaction conditions suitable for obtaining the product(s) indicated in FIG. 1A.

Optionally, the process for synthesizing the compound of Formula (Ia) can further include steps for isolating the intermediate compounds 03 and compound 06 prior to performing subsequent reactions. In addition, the compound of Formula (Ia) can optionally be converted to a pharmaceutically acceptable salt. In FIG. 1A, the conversion of the compound of Formula (I) to a pharmaceutically acceptable HCl salt of a compound of Formula (Ia) is shown according to Example 2.

The compound of Formula (Ib) is a second stereoisomer of Formula I.

Formula (Ib)

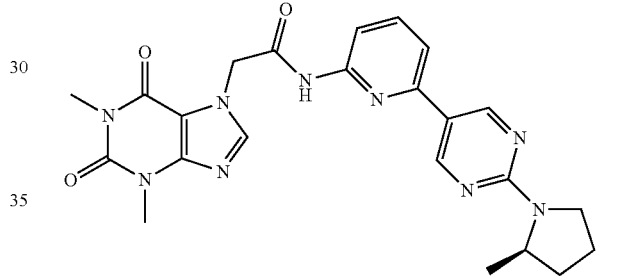

The compound of Formula (Ib) can be synthesized using a similar procedure as described above for making the compound of Formula (Ia), by substituting the use of (S)-2-methylpyrrolidine as a starting material in the synthesis of the compound of Formula (Ia) with (R)-2-methylpyrrolidine (i.e., substation of Compound $O_2$ in FIG. 1A with (R)-2-methylpyrrolidine). A racemic compound of formula (I) can also be prepared, for example, by using a racemic 2-methylpyrrolidine instead of Compound $O_2$ in the reaction scheme in FIG. 1A, or by combining a compound of Formula (Ia) with a compound of Formula (Ib). Compositions of Formula (I) comprising over 95% enantiomeric excess of the compound of Formula (Ia) over Formula (Ib) can be made by selecting (S)-2-methylpyrrolidine starting material with sufficient enantiomeric purity (i.e., greater than 95%). Similarly, compositions of Formula (I) comprising over 95% enantiomeric excess of the compound of Formula (Ib) over Formula (Ia) can be made by selecting (R)-2-methylpyrrolidine starting material with sufficient enantiomeric purity (i.e., greater than 95%). Compositions of Formula (I) having desired amounts of both stereoisomers of Formula (Ia) and Formula (Ib) can be made by combining pre-determined amounts of compositions of Formula (Ia) with greater than 95% enantiomeric purity with compositions of Formula (Ib) with greater than 95% enantiomeric purity, each made with 2-methylpyrrolidine starting material with the corresponding stereochemistry. The term "enantiomeric excess" a number from 0 to 100, zero being racemic and 100 being pure, single enantiomer. A compound which in the past might have been called 98% optically pure is now more precisely described as 96% ee.; in other words, a 90% e.e. reflects the presence of 95% of one enantiomer and 5% of the other in the material in question. A compound of Formula (I) can be obtained as a pharmaceutically acceptable salt.

The term, "pharmaceutically acceptable salts" of the compound of Formula (I) (e.g., Formula (Ia)), refers to salts prepared from pharmaceutically acceptable non-toxic acids including inorganic acids and organic acids. One particularly preferred salt form of the compound of Formula (I) (e.g., Formula (Ia)) is the hydrochloride salt disclosed in Example 2. In general, pharmaceutically acceptable salts of Formula (I) (e.g., Formula (Ia)) can be prepared to improve stability or toxicological properties of the compound, increase or decrease solubility, wetability, improve pharmacokinetic performance of the compound (e.g., $C_{max}$ or AUC measurements) or improve storage properties (e.g., to reduce hygroscopicity) of a pharmaceutical composition.

Inhibiting TRPA1 with the Compound of Formula (Ia)

The compound of Formula (Ia) is a novel small molecule antagonist of the TRPA1 channel as demonstrated by in vitro testing. The compound of Formula (Ia) and blocks inward currents through TRPA1 in rat, dog and human with an $IC_{50}$ of approximately 100 nanomolar (Table 1, data obtained according to Example 3). The antagonist effect of the compound of Formula (Ia) against hTRPA1 in a whole cell patch configuration was evaluated according to the method of Example 3.

TABLE 1

| CHANNEL | SPECIES | COMPOUND | TESTED CONCS. (nanomolar) | CURRENT ACTIVATION | $IC_{50}$ Inward current (nanomolar) |
|---|---|---|---|---|---|
| hTRPA1 | Human | Formula (Ia) | 10, 32, 100, 320, 1000 | 10 micromolar AITC | 93 ± 22 |
| rTRPA1 | Rat | Formula (Ia) | 32, 100, 320, 1000, 3200 | 10 micromolar AITC | 101 ± 8 |
| dTRPA1 | Dog | Formula (Ia) | 32, 100, 320, 1000 | 10 micromolar AITC | 102 ± 20 |

The compound of Formula (Ia) is highly selective for hTRPA1 as compared with TRP channels and voltage-gated ion channels. For example, when tested against eight different channels representing most of the ion channel families (Table 2, Example 3), none of the tested channels was reproducibly blocked or agonized by the compound of Formula (Ia) at physiologically relevant concentrations (e.g., 1, 3.2, 10, or 32 micromolar). Because the highest concentrations used (32 micromolar) had little effect, the actual $IC_{50}$ of the compound of Formula (Ia) for most of these channels cannot be determined. However, the compound of Formula (Ia) is at least 100-fold selective for block of TRPA1 over all other tested channels (Table 2, Example 3).

TABLE 2

| CHANNEL | TESTED CONCS. (micromolar) | CURRENT ACTIVATION | CURRENT EVALUATED | $IC_{50}$ (micromolar) | Fold Selectivity Compared to TRPA1 |
|---|---|---|---|---|---|
| hTRPV1 | 1, 10 | 500 nanomolar Capsaicin | Inward (−80 mV) | >10 | >100 |
| hTRPV3 | 1, 3.2, 10, 32 | 30 micromolar 2-APB | Inward (−80 mV) | >32 | >300 |
| hTRPV4 | 3.2, 10, 32 | 2 micromolar 4α-PDD | Inward (−80 mV) | 16 | ~170 |
| hTRPV4 Agonist | 3.2, 10, 32 | None | Inward (−80 mV) | No Effect | N/A |
| hTRPV6 | 1, 3.2, 10, 32 | Voltage | Inward (−80 mV) | 34 | ~370 |
| hTRPC5 | 1, 10 | 80 micromolar LaCl$_3$ | Inward (−80 mV) | >10 | >100 |
| hTRPM8 | 1, 3.2, 10, 32 | 100 micromolar Menthol | Inward (−80 mV) | 19 | ~200 |
| hERG | 1, 10 | Voltage | Tail current (−40 mV) | >10 | >100 |
| hNa$_v$1.2 | 1, 3, 10 | Voltage | Peak Inward (0 mV) | >10 | >100 |

The compound of Formula (Ia) is a novel small molecule antagonist of the human TRPA1 channel as demonstrated by in vivo testing. For example, the compound of Formula (Ia) was active in rodent models of pain in vivo induced by the TRPA1 channel with formalin injection.

The in vivo activity of the compound of Formula (Ia) can be compared to the activity of comparator compounds of Formula (II), Formula (III), and Formula (IV).

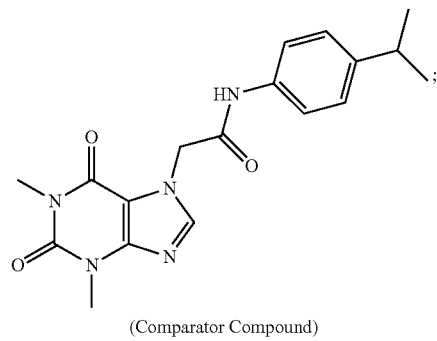

Formula (II)

(Comparator Compound)

Formula (III)

(Comparator Compound)

Formula (IV)

(Comparator Compound)

The compound of Formula (II) is a known TRPA1 inhibitor (see, e.g., U.S. Pat. No. 7,671,061) and was therefore used as a positive control. The compound of Formula (II) and methods of making and using this compound are disclosed as the TRPA1 inhibitor compound 200 in U.S. Pat. No. 7,671,061 (filed Dec. 22, 2006, issued Mar. 2, 2010).

Formula (II)

(Comparator Compound)

Figure 2:
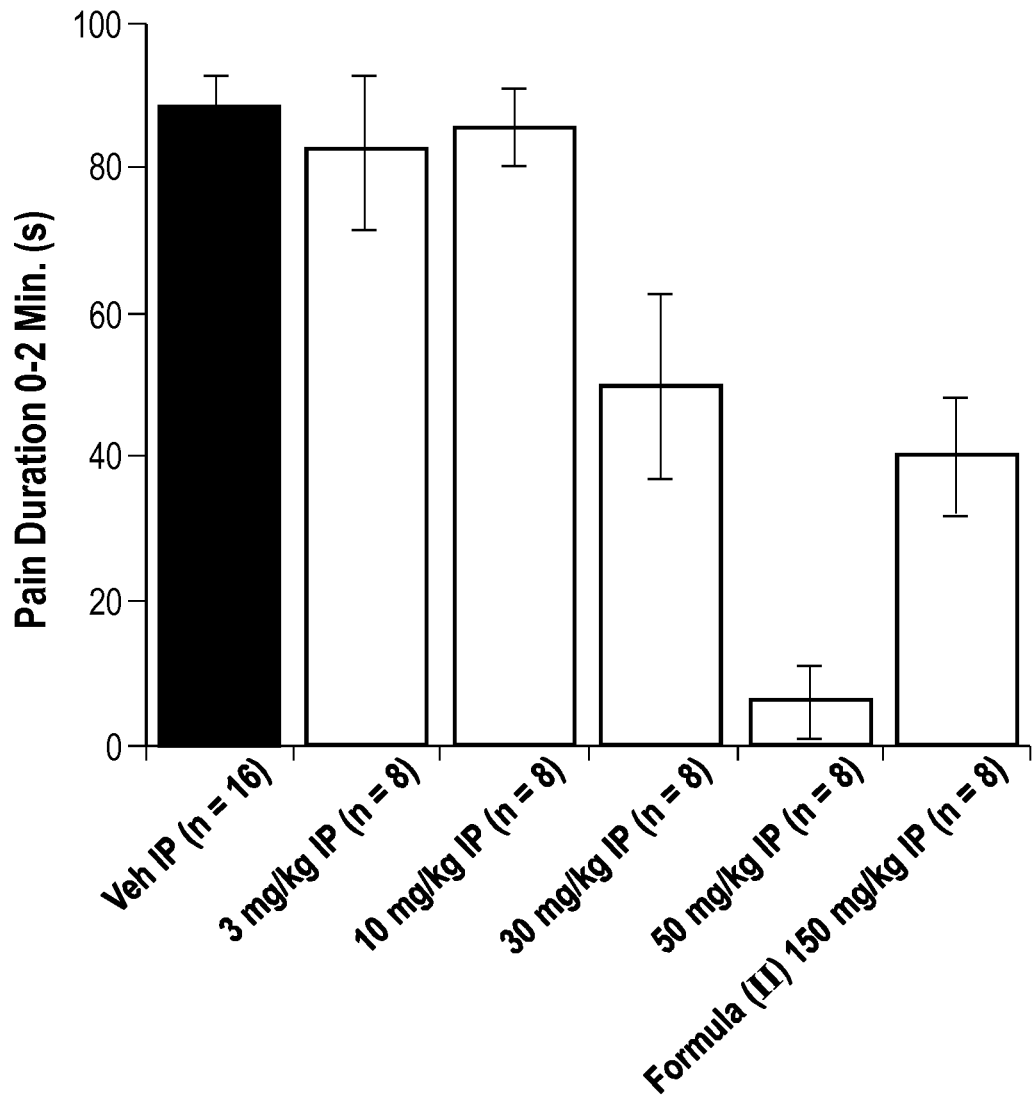
FIG. 2 is a bar graph demonstrating the effect of administering a pharmaceutical composition comprising the compound of Formula (Ia) at different concentrations (3, 10, 30, and 50 mg/kg) to rodents prior to conducting a formalin injection as described in Example 5.

The data shown in Tables 3a, 3b, and 3c and FIG. 2 were obtained by administering a pharmaceutical composition comprising the compound of Formula (Ia) to rodents in the formalin-induced pain duration at various doses according to Example 5. Specifically, the data in Tables 3a, 3b, and 3c and FIG. 2 were obtained by intraperitoneal (i.p.) administration of compositions containing different concentrations of the compound of Formula (Ia), a comparator composition containing recited amounts of the comparator compound (e.g., 150 mg/kg of the comparator compound of Formula (II) in Table 3a) and a control composition containing the vehicle (e.g., without the compound of Formula (Ia) or a comparator compound). As shown in Tables 3a, 3b, and 3c and FIG. 2, the animals treated with the compounds of Formulae (Ia), (II), and (III) showed shorter durations of pain behavior than those treated with the vehicle. This data demonstrates that the compound of Formula (Ia) has an analgesic effect on pain caused by TRPA1 activation with formalin.

TABLE 3a

| Compound and Dose | Duration of Pain Behavior (seconds) | Error (seconds) |
|---|---|---|
| Vehicle | 88.6 | 4.3 |
| 3 mg/kg Formula (Ia) | 82.3 | 10.6 |
| 10 mg/kg Formula (Ia) | 85.8 | 5.4 |
| 30 mg/kg Formula (Ia) | 49.8 | 12.8 |
| 50 mg/kg Formula (Ia) | 5.9 | 5.0 |
| 150 mg/kg Formula (II) | 40.0 | 8.1 |

TABLE 3b

| | Duration of Pain Behavior (seconds) | Error (seconds) |
|---|---|---|
| 50 mg/kg Formula (III) | 44.3 | 10.5 |
| Vehicle | 77.2 | 3.6 |

TABLE 3c

| | # of Flinches | Error |
|---|---|---|
| 300 mg/kg Formula (II) | 43 | 9 |
| 100 mg/kg Formula (II) | 62 | 17 |
| 30 mg/kg Formula (II) | 88 | 19 |
| Vehicle | 120 | 17 |
| Gabapentin (reference) | 75 | 13 |

Figure 3:
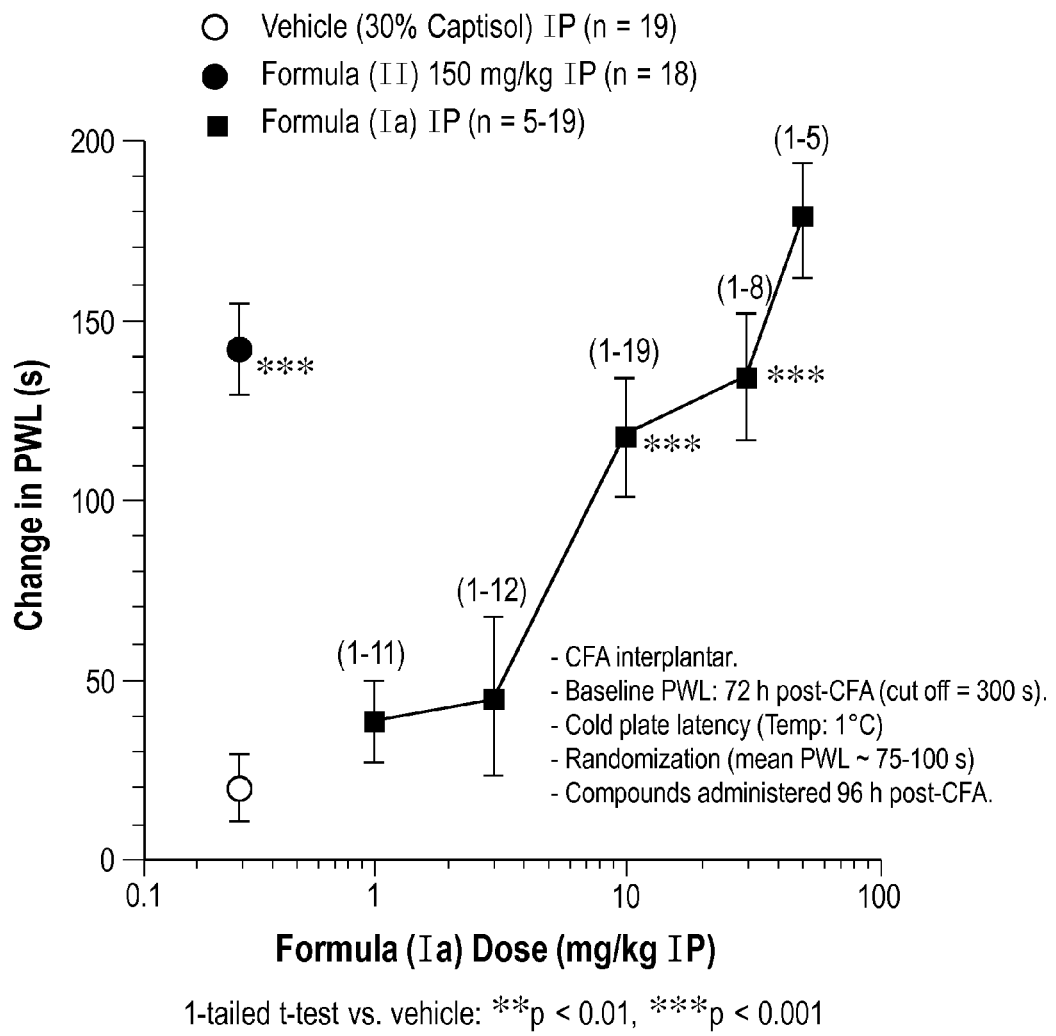
FIG. 3 is a line graph demonstrating increased Paw Withdrawal Latency (PWL) scores observed after i.p. administration of pharmaceutical compositions with increasing concentrations of the compound of Formula (Ia) in the Complete Freund's Adjuvant (CFA) rodent model described in Example 6.

The compound of Formula (Ia) is also active in rodent models of pain in vivo induced by cold allodynia following chronic Complete Freund's Adjuvant-induced inflammation, as described in Example 6. The data presented in Table 4 and FIG. 3 demonstrate increased Paw Withdrawal Latency (PWL) scores observed after i.p. administration of pharmaceutical compositions with increasing concentrations of the compound of Formula (Ia) in the Complete Freund's Adjuvant (CFA) rodent model described in Example 6. This data was obtained by measuring the change in PWL score as a function of the concentration of the compound of Formula (Ia), as well as the PWL scores observed upon administration of a composition containing the comparator compound of Formula (II) and a control with the vehicle containing a sulfobutylether β-cyclodextrin compound (available under the trade name Captisol® from CyDex Pharmaceuticals, Inc, Lenexa, Kans.). The data shows that the compound of Formula (Ia) has an analgesic effect on cold allodynia.

TABLE 4

| Compound and Dose | Change in Paw Withdrawal Latency | Error |
| --- | --- | --- |
| Vehicle | 19.8 | 9.4 |
| 1 mg/kg Formula (Ia) | 38.4 | 11.5 |
| 5 mg/kg Formula (Ia) | 45.0 | 22.0 |
| 10 mg/kg Formula (Ia) | 117.6 | 16.6 |
| 30 mg/kg Formula (Ia) | 134.4 | 17.8 |
| 50 mg/kg/ Formula (Ia) | 177.8 | 15.5 |
| 150 mg/kg Formula (II) | 142.2 | 12.3 |

Figure 4:
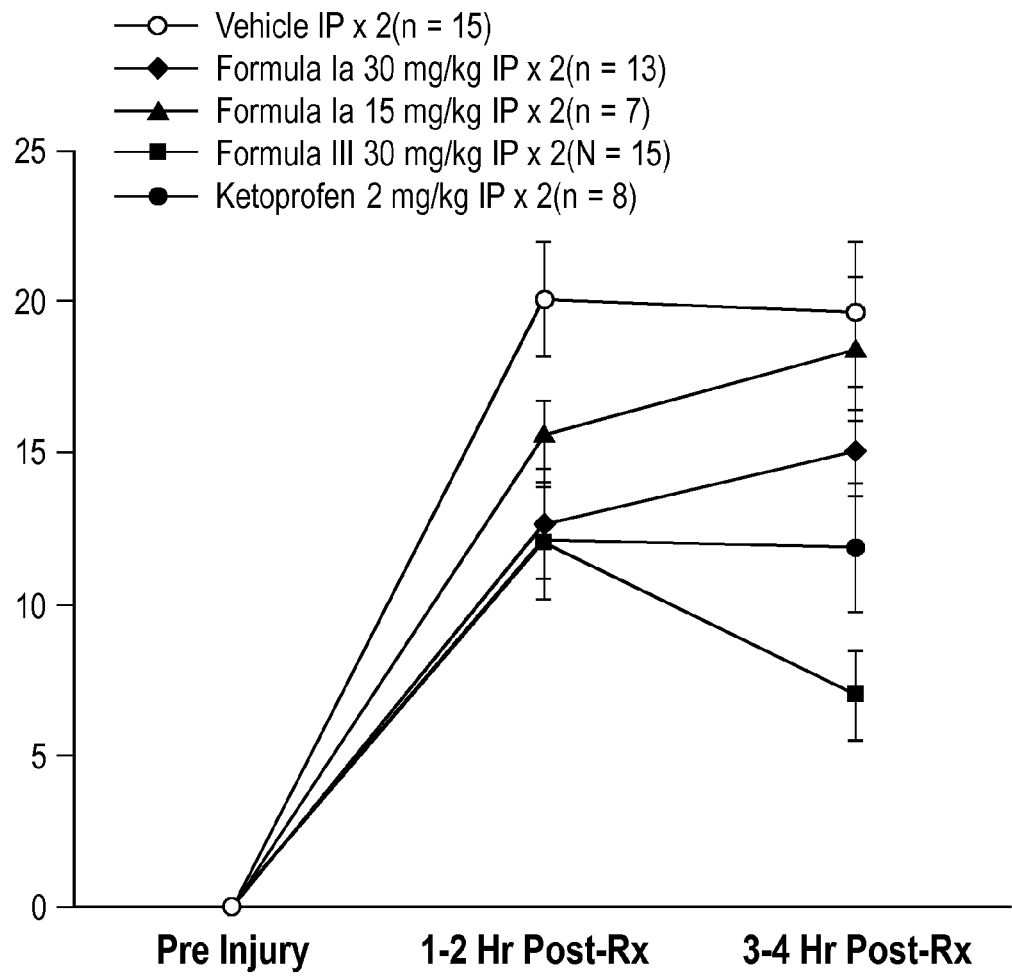
FIG. 4 is a line graph demonstrating reduction in guarding scores observed after i.p. administration of pharmaceutical compositions with various concentrations of the compound of Formula (Ia) in the rodent incisional pain model described in Example 7.

The compound of Formula (Ia) is also active in rodent models of pain in vivo induced by incision of the plantar surface of the hind paw (i.e., the "Brennan Surgical Model"), as described in Example 7. FIG. 4 shows the change in guarding score as a function of the administered concentration of the compound of Formula (Ia), as well as the guarding scores observed upon administration of the vehicle alone and comparator pharmaceutical compositions containing the comparator compound of Formula (III), or ketoprofen. Referring to FIG. 4 and Example 7, 60 mg/kg of the compound of Formula (Ia) delivered intraperitoneally (2 doses of 30 mg/kg before and immediately after the surgery) reduces spontaneous pain in the rodent incisional pain model described in Example 7 for up to 4 hours after surgery, better than ketoprofen (2 doses of 2 mg/kg intraperitoneally). Thirty (30) mg/kg of the compound of Formula (Ia) delivered intraperitoneally (2 doses of 15 mg/kg before and immediately after the surgery) reduces spontaneous pain for up to 2 hours after surgery (FIG. 4).

A comparator TRPA1 inhibitor of Formula (III) was also tested in the Brennan rodent model of Example 7 (FIG. 4). The comparator compound of Formula (III) and methods of making and using this compound are disclosed as the TRPA1 inhibitor compound 1 in PCT patent application PCT/US2009/069146 (published as WO2010/075353A1 on Jul. 1, 2010).

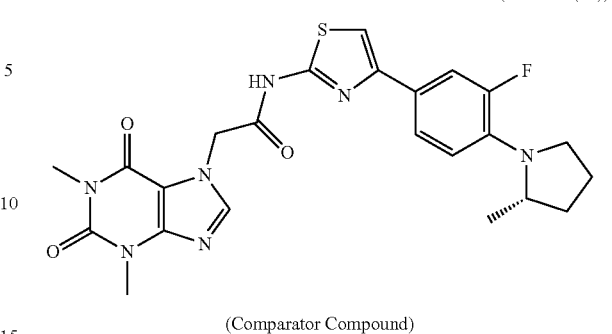

(Formula (III))

(Comparator Compound)

The in vitro TRPA1 activity of a comparator compound of Formula (IV) was measured:

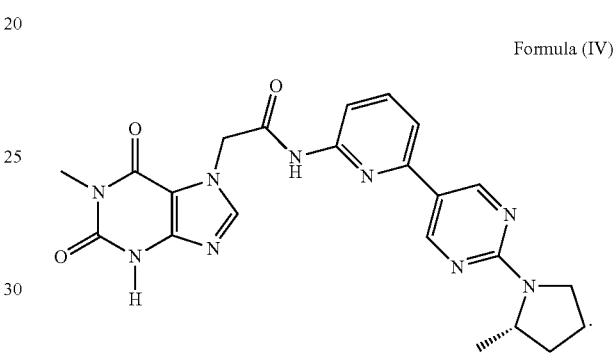

Formula (IV)

Figure 7:
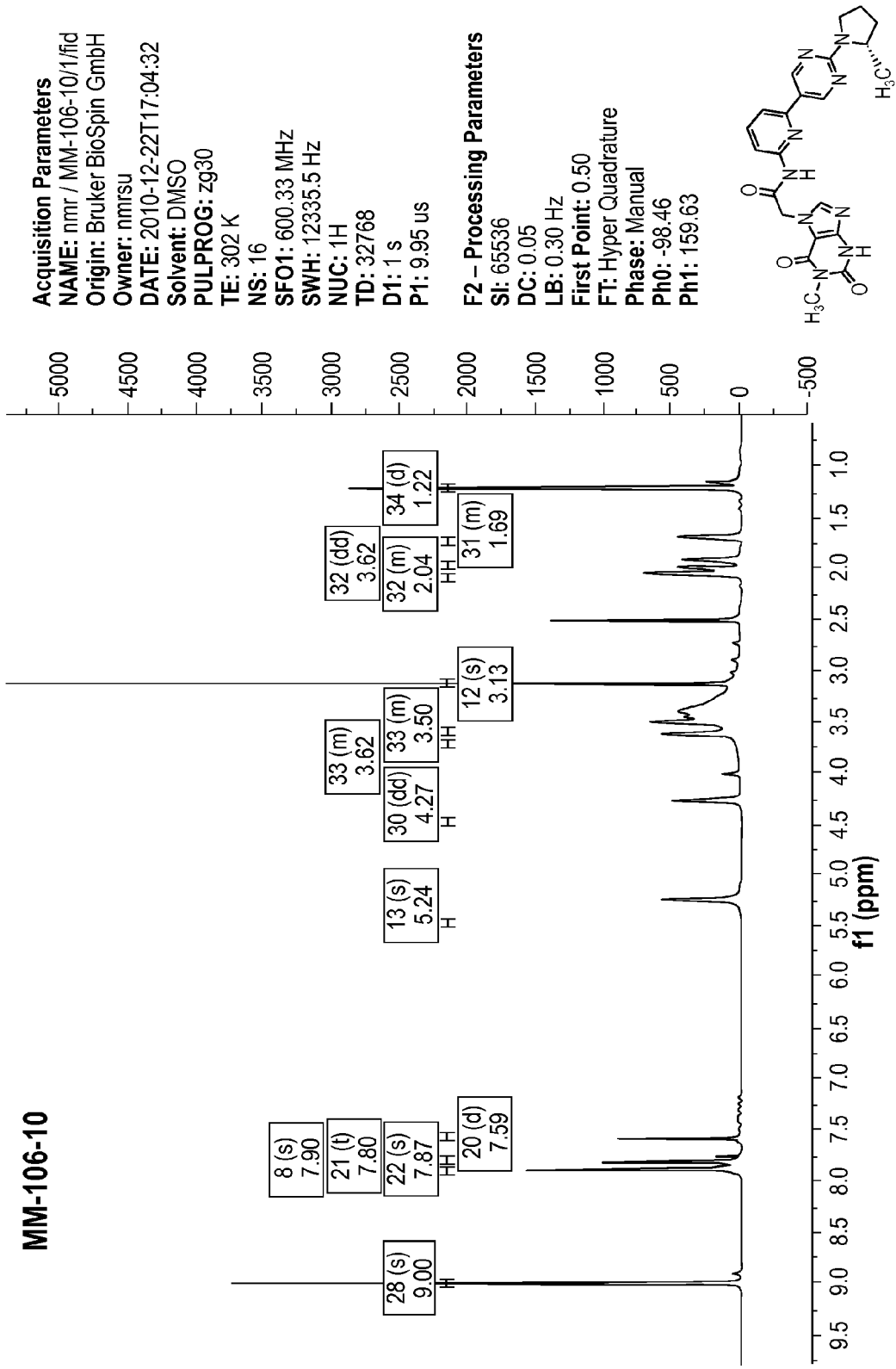
FIG. 7 is the characteristic NMR spectrum identifying the compound of Formula (Ib).

The chemical structure of the comparator compound of Formula (IV) was identified using nuclear magnetic resonance NMR. The NMR sample was prepared by dissolving approximately 1.85 mg of the metabolite of Formula (Ia) in 50 μL of NMR solvent. The sample was bath sonicated for 1 min to ensure proper dissolution before it was pipette into the NMR tube. The tube was sealed with a plastic ball and stored at room temperature prior to the experiments. NMR experiments were performed on a 600 MHz Brunker Avance III NMR Spectrometer equipped with a 1.7 nM Cryo-TCI probe. The sample was inserted into the magnet using a SampleJet accessory. In order to obtain complete connectivities for this molecule, a standard $^1$H-NMR spectrum, a multiplicity-edited $^1$H-$^{13}$C gHSQC spectrum, and a $^1$H-$^{13}$ gHMBC spectrum were recorded (FIG. 7). The comparator compound of Formula (IV) has a TrpA1 IC50 of 9.8 μM, and in vitro selectivity characterized by: TrpV3>10 μM, hERG>20 μM, NaV1.2>20 μM (Table 5). This data was collected using the same procedure as that of Example 3.

TABLE 5

| IC$_{50}$ in Patch Clamp Assay | |
| --- | --- |
| Assay | IC50 |
| TRPA1 | 9.8 μM |
| TrpV3 | >10 μM |
| hERG | >20 μM |
| NaV1.2 | >20 μM |

The compounds disclosed herein (e.g., a compound of Formula (I) or Formula (Ia)) can be used in assays for identifying compounds that inhibit TRPA1. For example, a method of identifying a TRPA1 inhibitor can include the steps of: contacting a test compound with a TRPA1 ion channel, measuring the inhibition of the TRPA1 ion channel by the test compound (e.g., generating a first IC50 value for the test compound), comparing the measurement of TRPA1 ion channel inhibition by the test compound with a second measurement of a second TRPA1 ion channel after contact with the compound of Formula (I) (e.g., measuring a second $IC_{50}$ value for the compound of Formula (I) or Formula (Ia)), and determining whether the test compound is a TRPA1 inhibitor by comparison of the first and second measurements of TRPA1 ion channel inhibition. The TRPA1 ion channel inhibition by the compound of Formula (I) (e.g., Formula (Ia)) (or compounds of Formula (II), (III), or (IV)) can be used as a comparator to the test compound. The measurement of TRPA1 ion channel inhibition can be performed by any suitable assay, including the assay of Example 3 (e.g., patch clamp protocol). In one embodiment, a method for identifying a TRPA1 ion channel inhibitor compound comprises contacting a TRPA1 protein in a cell-based assay, with a test agent to be tested for potential activity as a TRPA1 inhibitor; determining whether the test agent increases or decreases the activity of the TRPA1 protein; selecting for the agent that decreases the activity of the TRPA1 protein; determining the degree of TRPA1 inhibition of said agent that decreases the activity of the TRPA1 protein; and comparing the degree of TRPA1 inhibition of said agent that decreases the activity of the TRPA1 protein relative to the degree of TRPA1 inhibition observed by a reference agent, whereby an decrease in the degree of TRPA1 inhibition of said agent relative to the degree of TRPA1 inhibition by the reference agent thereby identifies said test agent as a TRPA1 Inhibitor. The reference agent can be (for example) a compound of Formula (Ia), (II), (III), or (IV).

The compound of Formula (Ib) is a second stereoisomer of Formula (I).

Formula (Ib)

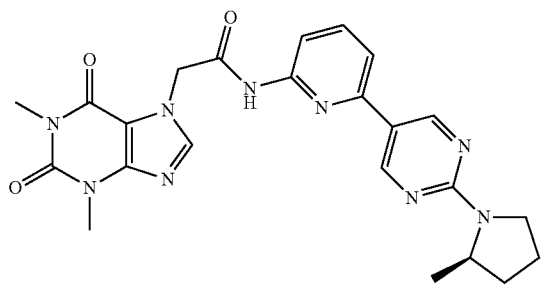

The compound of Formula (Ib) can be synthesized according Example 1c, and as a pharmaceutically acceptable salt. The compound of Formula (Ib) is a novel small molecule antagonist of the human TRPA1 channel in in vitro testing. The in vitro TRPA1 activity of compound of Formula (Ib) shown below was measured, having an $IC_{50}$ against hTRPA1 of between 50 and 100 nM as provided in Table 6 below.

In addition, the $IC_{50}$ for hTrpA1 measured in 1% RSA (rat serum albumin) was 15.2 uM for the compound of Formula (Ib), compared to 5.3 uM for the compound of Formula (Ia).

Pharmaceutical Compositions Comprising the Compound of Formula (I)

The compound of Formula (I) (e.g., a compound of Formula (Ia)) or a pharmaceutically acceptable salt thereof can be used in the manufacture of pharmaceutical compositions. Pharmaceutical compositions can be formed by combining the compound of Formula (I) (e.g., a compound of Formula (Ia)), or a pharmaceutically-acceptable salt thereof. The pharmaceutical composition can be formulated with a pharmaceutically-acceptable carrier suitable for delivery to a recipient subject (e.g., a human) in accordance with a desired method of drug delivery. Pharmaceutical compositions, particularly those formulated for oral delivery, preferably comprise the compound of Formula (I) (e.g., a compound of Formula (Ia)), or a salt of the compound of Formula (I) (e.g., a compound of Formula (Ia)), in an amount sufficient to achieve the intended purpose (e.g., the treatment or prevention of pain or other conditions responsive to inhibition or antagonism of the TRPA1 ion channel) and one or more additional carriers such as solubilizing agents (e.g., cyclodextrin and/or cyclodextrin derivatives), buffering agents, preservatives and the like (see, e.g., Example 10). The amount and concentration of compound of Formula (I) (e.g., a compound of Formula (Ia)) in the pharmaceutical composition, as well as the quantity of the pharmaceutical composition administered to a subject, can be selected based on clinically relevant factors, such as medically relevant characteristics of the subject (e.g., age, weight, gender, other medical conditions, and the like), the solubility of the compound in the pharmaceutical composition, the potency and activity of the compound, and the manner of administration of the pharmaceutical composition. For example, a pharmaceutical composition can be formulated for oral delivery of the compound of Formula (I) dissolved in a clinically-tolerated amount of a hydroxypropyl-beta-cyclodextrin (e.g., Formula (Ia) as shown in Example 10).

Pharmaceutical compositions may be formulated for a suitable route of administration for providing the patient with an effective dosage of a compound of the present invention. For example, oral administration may be employed (e.g., swallowed). Dosage forms include tablets, troches, dispersions, suspensions, solutions, capsules, patches, and the like. The most suitable formulation of a composition containing the compound of Formula (I) (e.g., a compound of Formula (Ia)) in any given case may depend on the severity of the condition being treated. The compositions may be conveniently presented in unit dosage form and prepared by any of the methods well known in the art of pharmacy. The compounds of Formula (I) (e.g., a compound of Formula (Ia)) may also be administered by controlled release means and/or delivery devices.

Pharmaceutical preparations can be prepared in accordance with standard procedures selected to treat a condition

TABLE 6

| CHANNEL | SPECIES | COMPOUND | TESTED CONCS. (nanomolar) | CURRENT ACTIVATION | $IC_{50}$ Inward current (nanomolar) |
|---|---|---|---|---|---|
| hTRPA1 | Human | Formula (Ib) | 10, 32, 100, 320, 1000 | 10 micromolar AITC | 77 | that is mitigated, eliminated, prevented or otherwise treated by the administration of a compound to inhibit the TRPA1 ion channel (see, e.g., Remington's Pharmaceutical Sciences, Mack Publishing Company, Easton, Pa. and Goodman, and Gilman's "The Pharmaceutical Basis of Therapeutics," Pergamon Press, New York, N.Y., the contents of which are incorporated herein by reference, for a general description of the methods for administering various therapeutic agents for human therapy). For example, the pharmaceutical compositions can be formulated for a desired route of administration, such as oral delivery. In particular, a medicament comprising a compound of Formula (I) (e.g., a compound of Formula (Ia)) can be formulated for oral administration for the therapeutic treatment of medical conditions, such as chronic or acute pain.

In preparing the compositions for oral dosage form, any of the usual pharmaceutical media may be employed as carriers, such as, for example, water, glycols, oils, alcohols, flavouring agents, preservatives, colouring agents, and the like in the case of oral liquid preparations (such as suspensions, solutions and elixirs) or aerosols; or carriers such as starches, sugars, micro-crystalline cellulose, diluents, granulating agents, lubricants, binders, disintegrating agents, and the like may be used in the case of oral solid preparations such as, for example, powders, capsules, and tablets, with the solid oral preparations being preferred over the liquid preparations. An example of a carrier is a cyclodextrin, for instance the sulfobutylether β-cyclodextrin compound available under the trade name Captisol® (CyDex Pharmaceuticals, Inc, Lenexa, Kans.). An example of a solid oral preparation is tablets or capsules containing the compound of Formula (I) (e.g., a compound of Formula (Ia)). If desired, tablets may be coated by standard aqueous or non-aqueous techniques.

The pharmaceutical compositions comprising one or more compounds of Formula (I) (e.g., a compound of Formula (Ia)) can be sterilized, for example, by filtration through a bacterial-retaining filter, or by incorporating sterilizing agents in the form of sterile solid compositions, which can be dissolved or dispersed in sterile water or other sterile injectable medium just prior to use.

Administration of Compositions Comprising the Compound of Formula (I)

Pharmaceutical compositions containing the compound of Formula (I) (e.g., a compound of Formula (Ia)) or pharmaceutically acceptable salts thereof can be used to treat or ameliorate medical conditions responsive to the inhibition of the TRPA1 ion channel in subjects (e.g., humans and animals). For example, the pharmaceutical compositions comprising a compound of Formula (I) (e.g., a compound of Formula (Ia)), or a pharmaceutically acceptable salt thereof, are useful as a perioperative analgesic, for example in the management of mild to moderate acute post-operative pain and management of moderate to severe acute pain as an adjunct to opioid analgesics. For example, a compound of Formula (Ia) can be used in the manufacture of a medicament for the treatment of pain. Optionally, the medicament can also include or be indicated for use in combination with a second compound selected from the group consisting of opioids, non-steroidal anti-inflammatory agents, calcitonin gene-related peptide (CGRP)-antagonists and steroids.

The compounds of Formula (I) (e.g., a compound of Formula (Ia)) may also be used in combination with the administration of opioid analgesics. For example, the pharmaceutical compositions comprising a compound of Formula (I) (e.g., a compound of Formula (Ia)), or a pharmaceutically acceptable salt thereof, are useful as a perioperative analgesic given in combination with an opioid analgesic, for example in the management of mild to moderate acute post-operative pain and management of moderate to severe acute pain as an adjunct to opioid analgesics.

The pharmaceutical compositions comprising a therapeutically-effective dose of the compound of Formula (I) (e.g., a compound of Formula (Ia)) can be administered to a patient for treatment of pain in a clinically safe and effective manner, including one or more separate administrations of the pharmaceutical compositions comprising the compound of Formula (I) (e.g., a compound of Formula (Ia)). For example, a pharmaceutical composition, when administered to a subject, results in an alanine aminotransferase (ALT) and/or aspirate aminotransferase (AST) level of less than about 250 mg/dL (e.g., about 200 mg/dL, 150 mg/dL, 100 mg/dL or 50 mg/dL) three days after administration.

The amount of active ingredients which can be combined with a carrier material to produce a single dosage form will vary depending upon the host being treated, the particular mode of administration. The amount of active ingredient that can be combined with a carrier material to produce a single dosage form will generally be that amount of the compound which produces a therapeutic effect. Generally, out of one hundred percent, this amount will range from about 1 percent to about fifty percent of active ingredient. In one embodiment, this amount is 1.6% (weight to weight). In another embodiment, this amount is 40% (weight to volume). Pharmaceutical compositions can contain, for example, 1 to 50% of a compound of Formula (I) (e.g., a compound of Formula (Ia)) in combination with a pharmaceutically acceptable carrier.

Pharmaceutical compositions containing the compound of Formula (I) (e.g., a compound of Formula (Ia)) or pharmaceutically acceptable salts thereof can be used to treat or ameliorate pain. Methods of treating medical conditions responsive to the inhibition of the TRPA1 ion channel in subjects (e.g., humans and animals) can include the administration of a therapeutically effective amount of the compound of the Formula (I) (e.g., a compound of Formula (Ia)) or a pharmaceutically-acceptable salt thereof. The pain can be chronic or acute. Methods of treatment can include administering to a subject in need thereof a therapeutically-effective amount of the compound of Formula (I) (e.g., a compound of Formula (Ia)) or a pharmaceutically acceptable salt thereof in one or more doses over a course of treatment. The pharmaceutical compositions comprising a therapeutically-effective dose of the compound of Formula (I) (e.g., a compound of Formula (Ia)) can be administered to a patient for treatment of pain in a clinically safe and effective manner, including one or more separate administrations of the pharmaceutical compositions comprising one or more compounds of Formula (I) (e.g., a compound of Formula (Ia)). For example, a pharmaceutical composition, when administered to a subject, results in an ALT and/or AST level of less than about 250 mg/dL (e.g., about 200 mg/dL, 150 mg/dL, 100 mg/dL or 50 mg/dL) three days after administration.

According to a further aspect, the invention provides the compound of Formula (I) (e.g., a compound of Formula (Ia)), or a pharmaceutically acceptable salt thereof, for the treatment or amelioration of pain or providing analgesia.

According to a further aspect, the invention provides the compound of Formula (I), or a pharmaceutically acceptable salt thereof, as a medicament.

In one example, the compound of Formula (I) (e.g., a compound of Formula (Ia)) can be orally administered to a subject human. The total daily dose of a compound of Formula (I) (e.g., a compound of Formula (Ia)) can be about 0.1 mg/kg/day to about 100 mg/kg/day of the compound of Formula (I) (e.g., a compound of Formula (Ia)) administered orally to a subject one to four times a day (e.g., QD, BID, TID, or QID) (e.g., 0.1 mg/kg/day to about 50 mg/kg/day). The total daily dose administered to a human can also be about 1 mg/kg/day to about 25 mg/kg/day, or about 3 mg/kg/day to about 10 mg/kg/day. The amount per administered dose or the total amount administered will depend on such factors as the nature and severity of the pain, the age and general health of the patient, and the tolerance of the patient to the compound.

A drug product comprising the compound of Formula (I) (e.g., a compound of Formula (Ia)) can be prepared by a suitable formulation process, e.g., wet granulation (see Remington pharmaceutical sciences). The pharmaceutical composition can be a unit dose in a shape to facilitate swallowing (e.g., a 0 or 00 size capsule). The unit dose can have an amount of the pharmaceutical composition ranging from 100 to 1600 mg in a size "00" capsule (e.g., from 100 to 800 mg) or equivalent tablet size. If 500 mg active/unit dose is achieved then development for that technology will be targeted to the highest achievable dose.

For example, a pharmaceutical composition comprising a therapeutically effective dose of the compound of Formula (I) (e.g., a compound of Formula (Ia)) or a pharmaceutically acceptable salt thereof can be administered (e.g., orally) to a subject in need thereof multiple times per day (e.g., BID) over a course of treatment of one or more days to treat pain in the subject.

EXAMPLES

Certain examples below illustrate the synthesis of the compound of Formula (I) (e.g., a compound of Formula (Ia)) and a pharmaceutically acceptable salt thereof. Further, the disclosure includes variations of the methods described herein to produce the compounds of Formula (I) (e.g., a compound of Formula (Ia)) that would be understood by one skilled in the art based on the instant disclosure.

Example 1A

Synthesis of the Compound of Formula (Ia)

Step 1

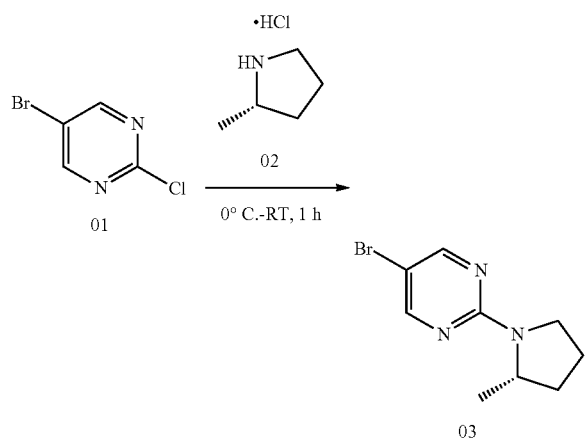

A dry 1 L round bottom flask charged with (S)-2-methylpyrrolidine (compound 02) (44.2 mL, 465 mmol) was cooled to 0° C. Compound 01 (60 g, 310 mmol) was added to the cooled amine compound 02 over 2 minutes (observed extreme exotherm). After addition was complete, the reactants were warmed to room temperature and continued to stir for 1 hr. Followed by liquid chromatography mass spectrometry (LCMS) and ultra-performance liquid chromatography (UPLC).

The resulting orange solids were dissolved in (9:1 DCM: MeOH, 200 mL), washed with saturated sodium bicarbonate 150 mL and water (3×100 mL). The combined aqueous layers were back extracted with (9:1 DCM:MeOH). The combined organic layers were washed with brine, dried over MgSO$_4$, and concentrated onto silica. The column was purified using a 400 g silica column with (Hex:EtOAc) solvent system (0% 4CV; 0-30% 6CV; 30% 6CV). The product eluted between 20-30% EtOAc. Fractions containing product were combined and dried under vacuum, the resulting clear oil was treated with hexanes, agitated, and then evaporated. A fine crystal formation was observed. The fine crystal formation was allowed to stand at 0° C. to aide white crystalline solids of compound 03.

For compound 03 in Step 1, Example 1: Isolated Yield: 67.2 g (89%) as white crystalline solids. (m/z M+=241); $^1$H NMR (300 MHz, DMSO) δ 9.01 (s, 1H), 8.42 (s, 2H), 4.20-4.06 (m, 1H), 3.56-3.34 (m, 2H), 2.12-1.81 (m, 3H), 1.68 (s, 1H), 1.16 (d, J=6.3 Hz, 3H).

Step 2

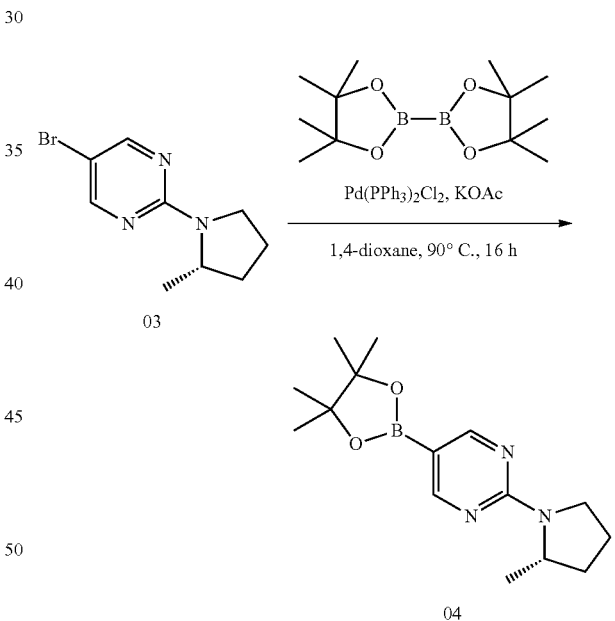

A 2 L three neck round bottom flask was charged with compound 03 (45 g, 186 mmol), bis(pinacolato)diboron (65.2 g, 257 mmol), bis(triphenylphosphine)palladium chloride (13.05 g, 18.59 mmol), potassium acetate (36.5 g, 372 mmol) and suspended in anhydrous 1,4-dioxane (Volume: 929 mL). The flask was flushed with nitrogen and the solids were fitted with reflux condenser and heated to 90° C. overnight.

1,4-dioxane was removed in vacuo. The crude material was dissolved in DCM (200 mL) and washed with water (3×100 mL). Combined aqueous layers back extracted with EtOAc. The combined organic layers were washed with brine, dried over MgSO$_4$, and concentrated onto silica. Material was split into two batches and column purified using 200 g silica column with Hex:EtOAc solvent system (0% CV; 3% 8CV; 5-20% 10CV; 20-50% 5CV). The starting material eluted with 3% EtOAc while desired product eluted between 5-40% EtOAc. Fractions containing product were combined and solvent was removed in vacuo to afford compound 04.

For compound 04 in Step 2, Example 1: Isolated Yield: 23.0 g (42%) as off-white solids. [(m/z=M+=289.20 (boronic acid observed at m/z 207.12)); $^1$H NMR (300 MHz, DMSO) δ 8.45 (s, 2H), 4.31-4.17 (m, 1H), 3.62-3.38 (m, 2H), 2.12-1.81 (m, 3H), 1.73-1.61 (m, 1H), 1.27 (s, 12H), 1.17 (d, J=6.3 Hz, 3H).

Step 3

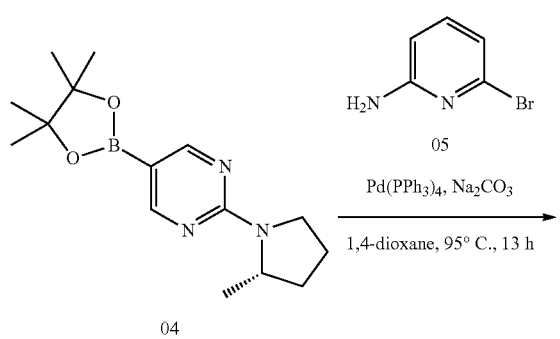

04

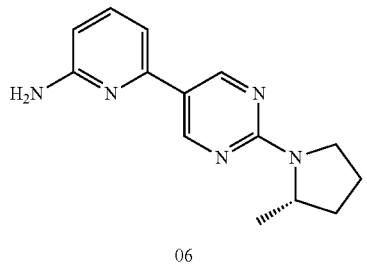

06

A 1 L round bottom flask was charged with compound 05 (15.14 g, 87 mmol), compound 04 (23.00 g, 80 mmol), purged with nitrogen, and followed by an addition of Pd(PPh$_3$)$_4$ (9.19 g, 7.95 mmol). The solids were suspended in a mixture of anhydrous 1,4-dioxane (398 ml) and aqueous 2M sodium carbonate (119 mL, 239 mmol). Reaction was heated to 95° C. for 13 hours.

Organics were separated from salts by transfer of liquid phase to 2 L round bottom flask. Salts were rinsed with 1,4-dioxane and combined with previously separated 1,4-dioxane solution. 1,4-dioxane was removed under vacuo. The yellow crude residue was dissolved in DCM and washed with water (3×100 mL), brine, and dried over MgSO$_4$ then concentrated onto silica. The column was purified using a 200 g silica column with DCM:EtOAc solvent system (0% 20CV; 20% 10 CV; 50-80% 10CV; 80% 5CV). The desired product eluted between 50-80% EtOAc. The fractions containing product were concentrated to isolate the compound 06.

For compound 06 in Step 3, Example 1: Isolated Yield: 13.7 g (67%) as light yellow solids. (m/z=M+=255.15); $^1$H NMR (300 MHz, DMSO) δ 8.88 (s, 2H), 7.40 (t, J=7.8 Hz, 1H), 6.95 (d, J=7.1 Hz, 1H), 6.35 (d, J=7.9 Hz, 1H), 5.96 (s, 2H), 4.31-4.19 (m, 1H), 3.66-3.41 (m, 2H), 2.13-1.84 (m, 3H), 1.75-1.65 (m, 1H), 1.22 (d, J=6.3 Hz, 3H).

Step 4

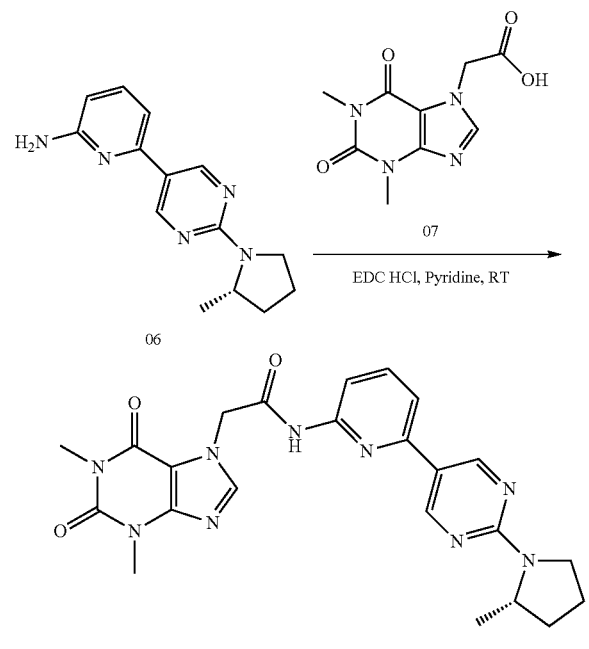

Formula (I)

A dry 200 mL round bottom flask was charged with compound 07 (12.17 g, 51.1 mmol), compound 06 (13.7 g, 53.7 mmol), EDC (19.59 g, 102 mmol) flushed with nitrogen followed by the addition of anhydrous pyridine (128 ml) (no exotherm observed). The suspension was stirred at room temperature for 1 h.

The reaction mixture was diluted with 100 mL water. An off-white precipitation was observed. The suspension was transferred to a 500 mL flask charged with stir bar and diluted with 150 mL 0.1M HCl while stirring. The precipitate turned light red in color forming an amorphous solid. Aqueous formulation was extracted with EtOAc (3×100 mL). The organic layer was washed with 0.1M HCl (3×50 mL), water, brine, and dried over MgSO$_4$ then concentrated onto silica. The column was purified using DCM:MeOH solvent system (0% 5CV; 0-3% 10CV; 3-4% 4CV; 4% 10CV). The product eluted between 3-4% MeOH. Appropriate fractions were pooled, and solvents were removed in vacuo, and was placed on high vacuum to afford the compound of Formula (Ia).

For the compound of Formula (Ia) in Step 4, Example 1: Isolated Yield: 20.7 g (85%) as off-white solids. The compound Formula (I) (m/z=M+=475), $^1$H NMR (300 MHz, DMSO) δ 10.95 (s, 1H), 9.01 (s, 2H), 8.09 (s, 1H), 7.82 (t, J=7.6 Hz, 2H), 7.61 (d, J=8.4 Hz, 1H), 5.32 (s, 2H), 4.33-4.23 (m, 1H), 3.71-3.49 (m, 2H), 3.47 (s, 3H), 3.20 (s, 2H), 2.18-1.84 (m, 3H), 1.70 (m, 1H), 1.24 (d, J=6.3 Hz, 3H).

Example 1B

Synthesis of Deuterated Compound of Formula (Ia)

Figure 1B:
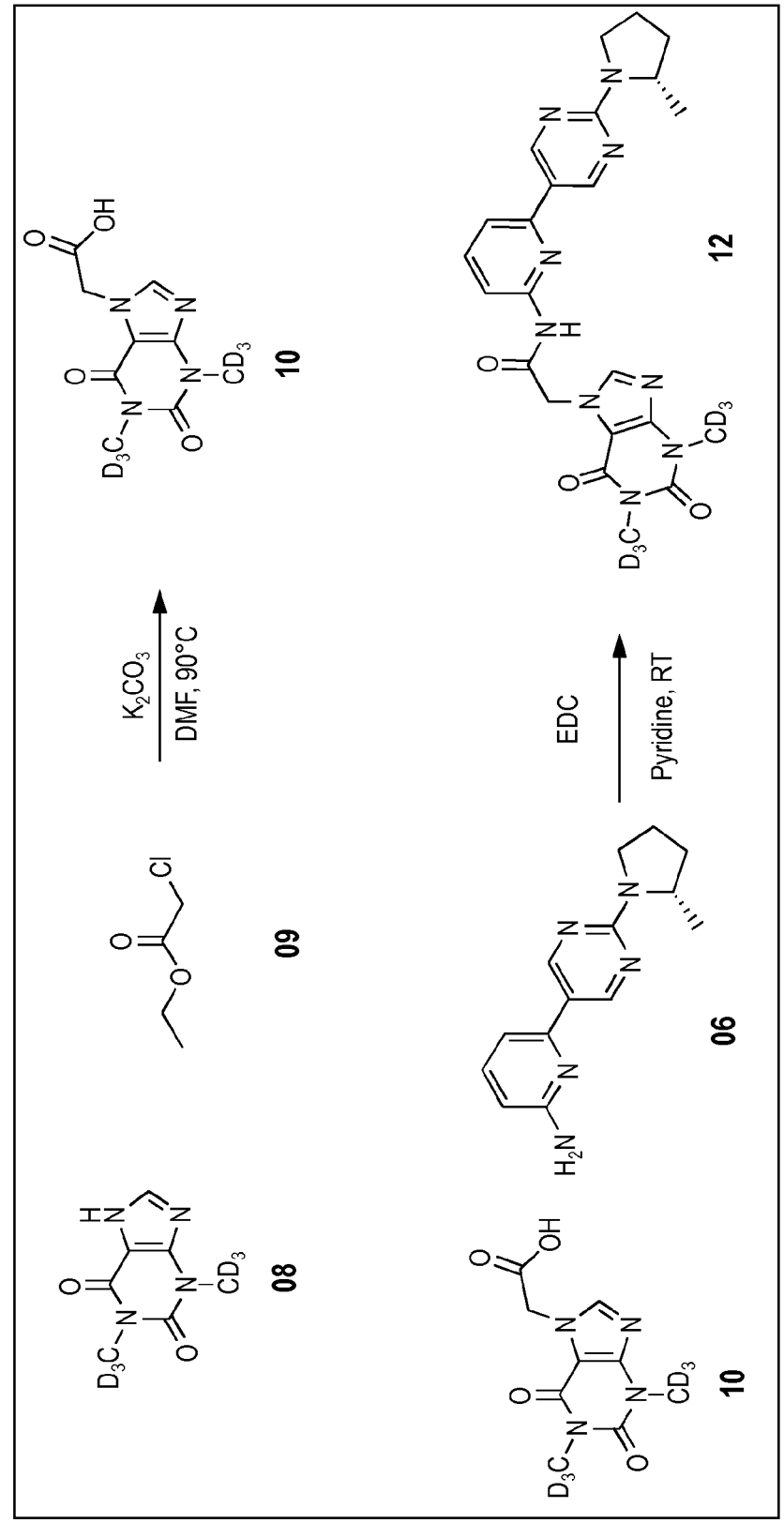
FIG. 1B is a reaction scheme to synthesize a deuterated compound (12), a deuterated analog of the compound of Formula (Ia), as described in Example 1B.

A deuterated compound (12) was prepared as described in FIG. 1B. Compound 10 was prepared from a commercial starting material compound 08 according to the following procedure:

Theophiline-d6 (0.480 g, 2.58 mmol) and potassium carbonate (0.392 g, 2.84 mmol), were suspended in DMF (12.89 mL), followed by addition of ethyl 2-chloroacetate (0.275 mL, 2.58 mmol) and heated to 90° C. for 1 hr. The reaction mixture was cooled to room temperature and diluted into 15 mL stirred water solution at room temperature. To the aqueous solution, lithium hydroxide (0.123 g, 5.16 mmol) in 10 mL water was added and continued to stir at room temperature for 1 hr. The solution was titrated to pH 4 with 5M HCl aq. The resulting white solids were collected via vacuum filtration to afford compound 10 (0.510 g, 81%) ESI-MS (EI+, m/z): 244.11

Deuterated compound 12 was synthesized in the same manner as Formula (Ia) using compound 06 (0.150 g, 0.609 mmol), and compound 10 (0.163 g, 0.640 mmol). The resulting crude solids were collected via vacuum filtration. Column purified by silica gel chromatography to afford deuterated compound 12 (0.135 g, 46%) ESI-MS (EI+, m/z): 481.25. $^1$H NMR (300 MHz, DMSO) δ 10.95 (s, 1H), 9.01 (s, 2H), 8.08 (s, 1H), 7.82 (t, J=7.7 Hz, 2H), 7.61 (d, J=8.5 Hz, 1H), 5.76 (s, 1H), 5.32 (s, 2H), 4.29 (s, 1H), 3.69-3.56 (m, 1H), 3.53 (s, 1H), 2.13-1.85 (m, 3H), 1.71 (d, J=2.3 Hz, 1H), 1.24 (d, J=6.3 Hz, 3H).

In addition to compound 12, the compounds described herein also include isotopes of the compound of Formula (I) (e.g., a compound of Formula (Ia)). For example, isotopes of Formula (I) (e.g., a compound of Formula (Ia)) can be formed as molecules formed by substitution of atomic isotopes at one or more of the atoms that constitute the compound of Formula (I) (e.g., a compound of Formula (Ia)). For example, the isotopes of Formula (I) may be radiolabeled with radioactive isotopes. Isotopes of Formula (I) (e.g., a compound of Formula (Ia)) include compounds formed by substitution of hydrogen in Formula (I) (e.g., a compound of Formula (Ia)) with deuterium ($^2$H), or tritium ($^3$H), or substitution of one or more carbon atoms in Formula (I) (e.g., a compound of Formula (Ia)) with carbon-13 ($^{13}$C) or carbon-14 ($^{14}$C). Preferred isotopes of Formula (I) (e.g., a compound of Formula (Ia)) inhibit TRPA1 in humans or animals. All isotopic variations of the compounds disclosed herein, whether radioactive or not, are intended to be encompassed within the scope of the present invention. For example, deuterated compounds or compounds containing $^{13}$C are intended to be encompassed within the scope of the invention.

Example 1C

Synthesis of the compound of Formula (Ib) (the enantiomer of Formula (Ia))

Formula (Ib)

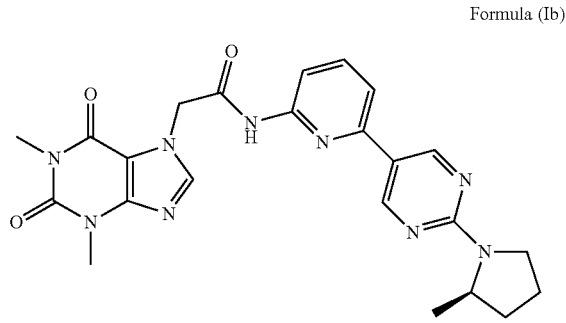 [SMILES: C[C@@H]1CCCN1c1ncc(-c2cccc(NC(=O)Cn3cnc4c3c(=O)n(C)c(=O)n4C)n2)cn1]

The compound of Formula (Ib) (enantiomer of Formula Ia) was synthesized using an identical procedure as described above, with the one difference being the use of (R)-2-methylpyrrolidine as a starting material in step 1 instead of (S)-2-methylpyrrolidine (Compound O$_2$ in FIG. 1A). The yield in the last step is 92%, as white powder. $^1$H NMR (300 MHz, DMSO-d6) δ 10.95 (s, 1H), 9.01 (s, 2H), 8.09 (s, 1H), 7.82 (t, J=7.7 Hz, 2H), 7.61 (d, J=8.5 Hz, 1H), 5.32 (s, 2H), 4.47-4.13 (m, 1H), 3.72-3.58 (m, 2H), 3.27 (s, 3H), 3.20 (s, 3H), 2.17-1.86 (m, 3H), 1.71 (s, 1H), 1.24 (d, J=6.3 Hz, 3H). LCMS (m/z=M+H=476).

The IC$_{50}$ for hTrpA1 measured in 1% RSA was 15.2 uM for formula (Ib), compared to 5.3 uM for the compound of Formula (Ia).

Example 2

Formation of the HCl Salt of a Compound of Formula (Ia)

1M HCl in EtOH: A 500 mL flask was charged with stir bar, and 185 mL 200 proof EtOH at 0° C. Acetyl chloride (14.20 mL, 200 mmol) was then added and stirred at 0° C. for five minutes, then at room temperature for 10 minutes.

HCl Salt Precipitation: To a 1 L round bottom flask was charged with the dry compound of Formula (I) (20.5 g, 43.1 mmol) and 200 mL 1M HCl in EtOH (freshly made) was added and stirred at room temperature for 1 hr. The suspension went from a mostly homogenous clear yellow to white solid suspension in light yellow solvent. After 1 hr, solids were collected via vacuum filtration with aide of EtOH, then rinsed with EtOH (3×100 mL) and placed on high vacuum overnight. After 18 hours, material was removed from high vacuum and transferred to amber jar.

For Example 2, HCl Salt Isolated Yield: 22.6 g (>100%) as an off-white solid. (I) salt (m/z=M+=475), $^1$H NMR (300 MHz, DMSO) δ 10.95 (s, 1H), 9.01 (s, 2H), 8.09 (s, 1H), 7.82 (t, J=7.6 Hz, 2H), 7.61 (d, J=8.4 Hz, 1H), 5.32 (s, 2H), 4.33-4.23 (m, 1H), 3.71-3.49 (m, 2H), 3.47 (s, 3H), 3.20 (s, 2H), 2.18-1.84 (m, 3H), 1.70 (m, 1H), 1.24 (d, J=6.3 Hz, 3H). Elemental analysis: C, 50.54 (cal. 53.96); H, 5.34 (cal. 5.12); Cl, 6.34 (cal. 6.92); N, 22.69 (cal. 24.62); O, 9.38.

Example 3

Measuring In Vitro Inhibition of TRPA1

The in vitro inhibition of TRPA1 of the compound of Formula (Ia) was tested using the procedure outlined in del Camino et al., J. Neurosci., 30(45):15165-15174, incorporated herein by reference and described below. Data for TRPA1 inhibition and the selectivity of TRPA1 inhibition was obtained by this method for the compound of Formula (Ia) and included in Table 1 and Table 2. All currents were recorded in whole-cell configuration using EPC-9 and EPC-10 amplifiers and Patchmaster software (HEKA). Patch pipettes had a resistance of 1.5-3 MΩ and 60-75% of the series resistance was compensated. The standard pipette solution consisted of 140 mM CsAsp, 10 mM EGTA, 10 mM HEPES, 2.27 mM MgCl$_2$, 1.91 mM CaCl$_2$, 4 mM MgATP, and 0.1-0.3 mM Na$_2$GTP, with pH adjusted to 7.2 with CsOH. In addition, a solution containing 145 mM CsCl, 10 mM HEPES, 10 mM EGTA and 1 mM MgCl$_2$ (pH 7.2 adjusted with CsOH) can be used. The standard bath solution contained 150 mM NaCl, 10 mM HEPES, 10 mM glucose, 4.5 mM KCl, 1 mM EGTA, 3 mM MgCl$_2$, with pH adjusted to 7.4 with NaOH. In some instances, 2 mM $CaCl_2$ was added in place of EGTA and the concentration of $MgCl_2$ was reduced to 1 mM.

Data were collected either by continuous recordings at −60 mV or by applying voltage ramps from a holding potential of 0 mV every 4 s. Continuous recordings were collected at 400 Hz and digitally filtered off-line at 10 Hz for presentation. Voltage ramps were applied from −100 mV to 100 mV over the course of 400 ms, and data were collected at 10 kHz and filtered at 2.9 kHz. Inward and outward currents were analyzed from the ramps at −80 and 80 mV, respectively. Liquid junction potential correction was not used.

Solutions were switched using a gravity-fed continuous focal perfusion system. To achieve rapid temperature changes, two temperature control and perfusion systems were employed simultaneously. For temperatures≥22° C., a Warner Instruments bipolar temperature controller (TC-344B) and inline heater (SHM-8) were used. For temperatures below 22° C. a Warner Instruments temperature controller (CL-100) and thermal cooling module (TCM-1) were used. Temperatures were confirmed using a thermistor (Warner Instruments, TA-29), with temperatures at the recorded cell estimated to be within +/−2° C. of those reported.

$IC_{50}$ of compounds was estimated by testing each compound at 5 micromolar and 500 nanomolar. When 5 micromolar compound showed no block, $IC_{50}$ was estimated as >10 micromolar. When 5 micromolar compound showed 50% or less block, a rough estimate of $IC_{50}$ in the range of 5-10 micromolar could be made. $IC_{50}$ for compounds between 500 nanomolar and 5 micromolar was similarly estimated. Compounds blocking 50% or more at 500 nanomolar are retested at multiple concentrations, and the % block at each is fitted by standard equations to determine $IC_{50}$ accurately using a 5-6 point concentration/response experiment.

Example 4

Evaluating the In Vivo Efficacy of TRPA1 Inhibitor Compounds

The compound of Formula (Ia) was evaluated for activity in vivo. In some examples, comparator TRPA1 inhibitor compounds of Formula (II) or Formula (III) were also evaluated, as described in the examples below.

The comparator compound of Formula (II) and methods of making and using this compound are disclosed as the TRPA1 inhibitor compound 200 in U.S. Pat. No. 7,671,061 (filed Dec. 22, 2006, issued Mar. 2, 2010) and are incorporated herein by reference in their entirety.

The comparator compound of Formula (III) and methods of making and using this compound are disclosed as the TRPA1 inhibitor compound of Formula (I) in PCT patent application PCT/US2009/069146 (published as WO2010/075353A1 on Jul. 1, 2010) and are incorporated herein by reference in their entirety.

The potency and pharmacokinetic (PK) properties of (a) the compound of Formula (Ia); and (b) comparator compound of Formula (III) were evaluated. Bioavailability was measured as well. A pharmacokinetic study was performed to obtain a plasma drug concentration vs time plot for the drug after both intravenous (IV) and oral (PO) administration. The absolute bioavailability is the dose-corrected area under curve (AUC) non-intravenous divided by AUC intravenous. The formula for calculating F for a drug administered by the oral route (PO) is given below.

The bioavailability was calculated using the equation shown below:

% $F$=AUC PO×Dose IV/AUC IV×Dose PO

Human Plasma Protein Binding

The amount of compound in buffer (free fraction) and the amount of compound associated with the plasma fraction is determined by equilibrium dialysis; the amount of compound bound is expressed as a percentage. (Banker et al., *Journal of Pharmaceutical Sciences* (2003) 92(5): 967-74.)

In Table 6, an "A" indicates an $IC_{50}$ of less than 25 nanomolar; a "B" indicates an $IC_{50}$ of 25 nanomolar to less than 50 nanomolar; a "C" indicates an $IC_{50}$ of 50 nanomolar to less than 100 nanomolar; a "D" indicates an $IC_{50}$ of 100 nanomolar or greater.

While the compound of Formula (III) was more potent in vitro, the compound of Formula (Ia) has in vivo properties that make it advantageous over the compound of Formula (III). Greater protein binding was observed for the Compound of Formula (III) than the compound of Formula (Ia). $IC_{50}$ for the compound of Formula (Ia), when tested against hTRPA1, was between 50 and 100 nanomolar. The compound of Formula (Ia) was less than 99% protein-bound and the bioavailability for fed rats was greater than 50%. Although the $IC_{50}$ for the compound of Formula (III), when tested against hTRPA1, was between 0 and 25 nanomolar. The compound of Formula (III) was greater than 99% protein-bound and the bioavailability for fed rats was between 1 and 25%.

TABLE 6

| Parameter | Formula (III) | Formula (Ia) |
|---|---|---|
| Potency ($IC_{50}$) | | |
| Human | A | C |
| Rat | C | D |
| Dog | A | D |
| Bioavailability (Rat) | | |
| Fed | Between 1 and 25% | Greater than 50% |
| Fasted | Between 25 and 50% | Between 25 and 50% |
| Human Plasma Protein Binding | Greater than 99% | Less than 99% |

In addition, as shown in Table 6 above, the compound of Formula (Ia) demonstrates less of a fed/fasted effect than the compound of Formula (III). Compounds with reduced fed/fasted effects in humans can lead to increased patient compliance. In addition, the compound of Formula (Ia) is less protein-bound than the compound of Formula (III). As a consequence, more of the compound is available to be distributed to the target tissues upon administration.

Example 5

Formalin-Induced Pain Behavior In Vivo Rodent Model

The compound of Formula (Ia) and the comparator compounds of Formula (II) and Formula (III) were tested in the formalin-induced pain test reported by Dubuisson et al., Pain 1977 December; 4(2):161-74 (incorporated herein by reference in its entirety). Dubuisson et al. (1977) describe a method for assessing pain and analgesia in rats and cats. Briefly, dilute formalin (50 μL of 3% formalin) is injected into the plantar surface of the hind paw. The animal is promptly returned to an observation arena (standard Plexiglass rat cage), at which point a trained observer records the time the animal spends exhibiting pain behaviors (flinching, licking, biting of the injected paw/leg) for a period of 5 minutes. The individual responsible for counting the pain behaviors in a particular study is blinded to the treatment groups.

Rats were treated with the HCl salt of Compound (Ia) at various doses (3, 10, 30, and 50 mg/kg, IP) or with the vehicle (IP). The vehicle animals showed an average of about 88.6 seconds exhibiting pain behaviors (e.g., flinching, lifting and licking the paw). Results are shown in FIG. 2 and Table 3a. The animals treated with Formula (Ia) showed a range of 5.9 to 85.8 seconds exhibiting pain behaviors. Results are shown in FIG. 2 and Table 3a. Results of Formula (II) effects on formalin induced responses are shown in Tables 3a and 3c. The animals treated with Formula (III) exhibited pain behaviors for 44.3 seconds compared to vehicle at 77.2 seconds. Results are shown in Table 3b.

Example 6

Complete Freund's Adjuvant (CFA) Inflammatory In Vivo Rodent Pain Model

The compound of Formula (Ia), the comparator compound of Formula (II) and ketoprofen were tested by the CFA-induced pain test method reported in del Camino et al., J. Neurosci., 30(45):15165-15174, incorporated herein by reference in its entirety.

Briefly, the hind paw is sensitized to cold temperature (allodynic), by administering 0.1 mL of Complete Freund's Adjuvant (CFA) is administered to the left hind paw. 2-3 days later, the time taken for the animal to lift its CFA-injected paw is recorded compared to its un-injected normal right hind paw. Animals are placed on the surface of the cold plate (1° C.) and the operator stops testing at the instant when the animal displays discomfort by flinching or lifting its paw from the plate (paw withdrawal latency, or PWL). To avoid tissue damage the maximum cut-off time is 5 minutes. Animals that are allodynic (average PWL to the first three pain behaviors<150 seconds for the CFA-injected hind paw: ~≥50% difference between the normal and CFA-injected paw) are included in the study and subsequently randomized across treatment groups. The following day, the animals are dosed under blinded conditions. Following the 1-2 hour pretreatment time, the post-dose PWL readings are again taken. The efficacy of the drug treatment is assessed by comparing the PWL in the drug treatment animals to those animals that receive the vehicle.

Example 7

Surgical Incision Pain Behavior In Vivo Rodent Model (FIG. 4)

The compound of Formula (Ia), the comparator compound of Formula (III) and ketoprofen were tested by the incisional pain test method reported in Brennan et al., Pain, 1996 March; 64(3):493-501 incorporated herein by reference in its entirety. Briefly, in rats under anesthesia, a 1 cm incision through skin and underlying muscle is made in the bottom of one hind paw. The incision is sutured closed and the animals allowed to regain consciousness in their home cage before being placed on a special mesh rack. The blinded observer subjectively assesses and records each animal's pain score every 5 minutes for 1 hour. Pain scores are assigned as follows: Score of 0=Injured paw is held flat on the rack and is bearing weight (=uninjured paw); 1=Injured paw is slightly lifted from the rack but is bearing some weight; 2=Injured paw is flat but is bearing no weight, or heel is lifted high off the rack with only toes touching. At the end of each hour, pain scores are added up and the final score recorded (maximum score=39). In a typical study the efficacy of the drug treatment is determined by comparing the cumulative guarding scores at 1-2 and 3-4 hours following surgical injury to the cumulative guarding scores of animals that received the vehicle.

Sixty (60) mg/kg delivered intraperitoneally (2 doses of 30 mg/kg before and immediately after the surgery) reduced spontaneous pain for up to 4 hours after surgery, equivalent to ketoprofen (2 doses of 2 mg/kg intraperitoneally). Thirty (30) mg/kg compound of Formula (Ia) intraperitoneally (2 doses of 15 mg/kg before and immediately after the surgery) only reduced spontaneous pain for up to 2 hours after surgery.

Example 8

Hepatotoxicity Serum Biomarker Study of the Compound of Formula (I) and a Comparator Compound of Formula (III)

Figure 5A:
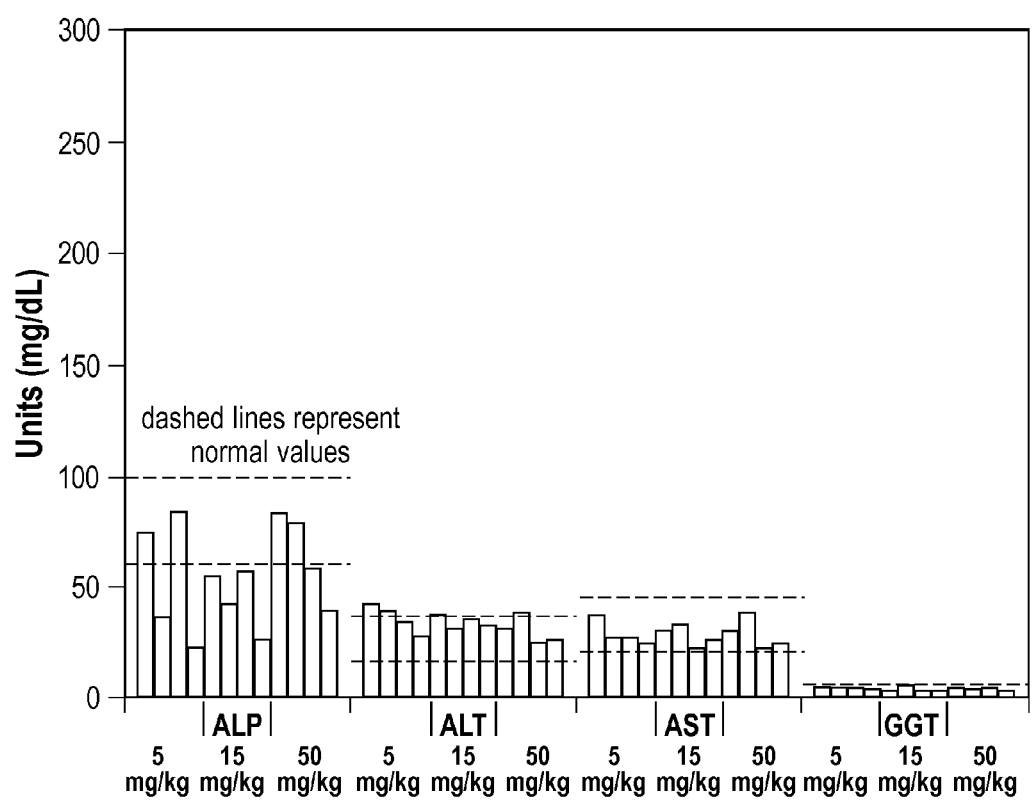
FIG. 5A is a bar graph of data for measurement of serum chemistry biomarkers of hepatotoxicity measured in female dogs orally dosed with a compound of Formula (Ia). The figures along the X-axis are the doses of compound of Formula (I) administered.

The compound of Formula (Ia) was orally dosed to female dogs at dose levels of 5, 15 or 50 mg/kg using 30% Sulfobutylether β-cyclodextrin as the vehicle for assessment of safety as measured via serum chemistry biomarkers of hepatotoxicity or bile duct injury FIG. 5A, showing measurements of alanine aminotranferease [ALT], aspartate aminotranferease [AST], alkaline phosphatase [ALP] and gamma-glutamyl transferase [GGT] in the dogs at each dose level (each bar represents a measurement from 1 dog in the study). The data in FIG. 5A shows that the compound of Formula (Ia) did not elevate serum biomarkers of hepatotoxicity or acute phase response when dosed at 50 mg/kg PO (oral).

Figure 5B:
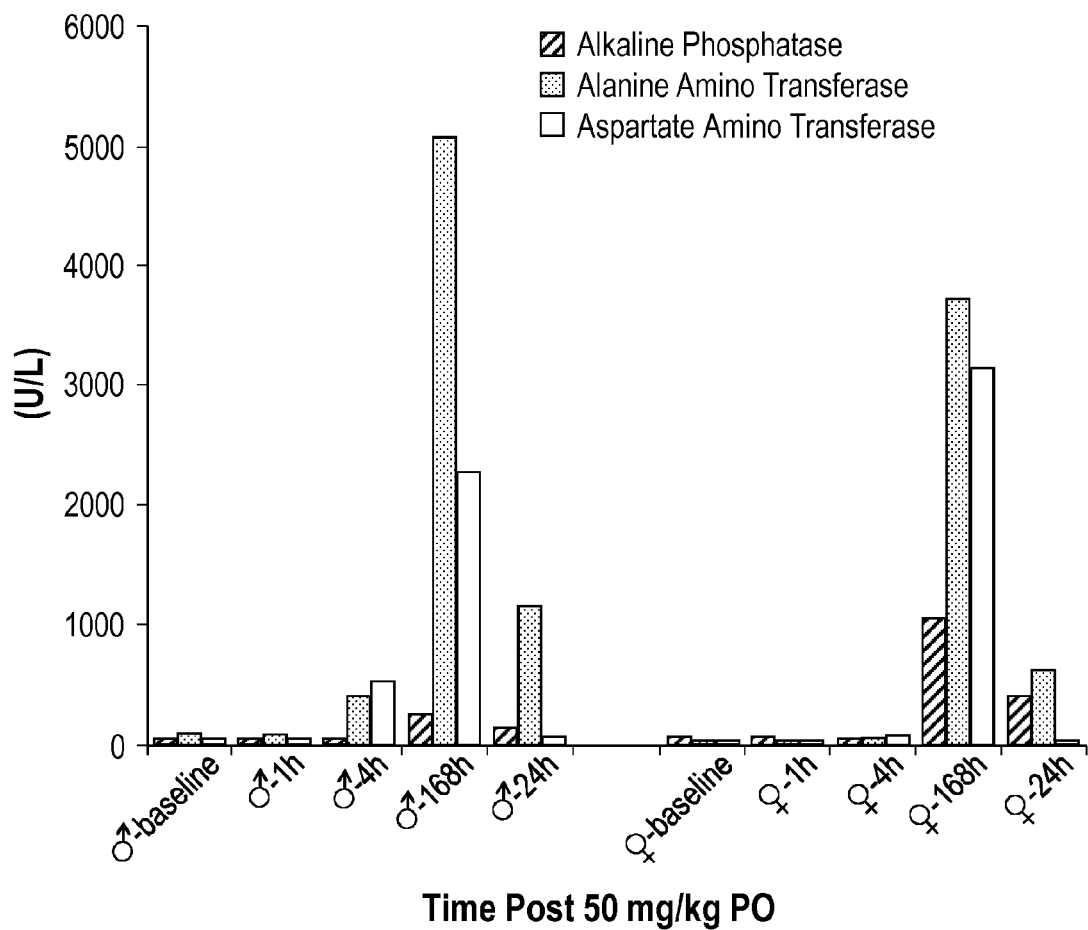
FIG. 5B is a bar graph of data for measurement of serum chemistry biomarkers of hepatotoxicity measured in male and female dogs orally dosed with a comparator compound of Formula (III).

In contrast, the data in FIG. 5B shows that the comparator compound of Formula (III) did elevate serum biomarkers of hepatotoxicity. For example, the ALT levels were elevated up to about 60-fold in male dogs and up to about 130-fold in female beagle dogs following a single PO dose of 50 mg/kg.

Example 9

Rodent Repeat Dose Toxicity Studies, Intraperitoneal (i.p.)

The compound of Formula (Ia) was evaluated in a 7-day repeat dose screening toxicity study in female rats. In order to maximize systemic exposure, rats were administered compound of Formula (Ia) i.p. at 50 mg/kg/day for 7 consecutive days, to obtain the results shown in FIG. 6. Clinical chemistry parameters were evaluated on Days 3 and 8. Histopathology was performed on select organs including the liver, kidney, spleen, and lung. After administration of the compound of Formula (Ia) at the 50 mg/kg IP dose, no adverse clinical signs, changes in body weight, or changes in clinical chemistry parameters were noted. No histopathological findings in the liver, kidney, spleen, or lung were observed after administration of the compound of Formula (Ia).

According to the pathologist's report, no adverse effects related to the compound of Formula (Ia) were identified in sections of liver harvested on study days 3 and 8 or spleen, kidney and lung harvested on study day 8.

Figure 6:
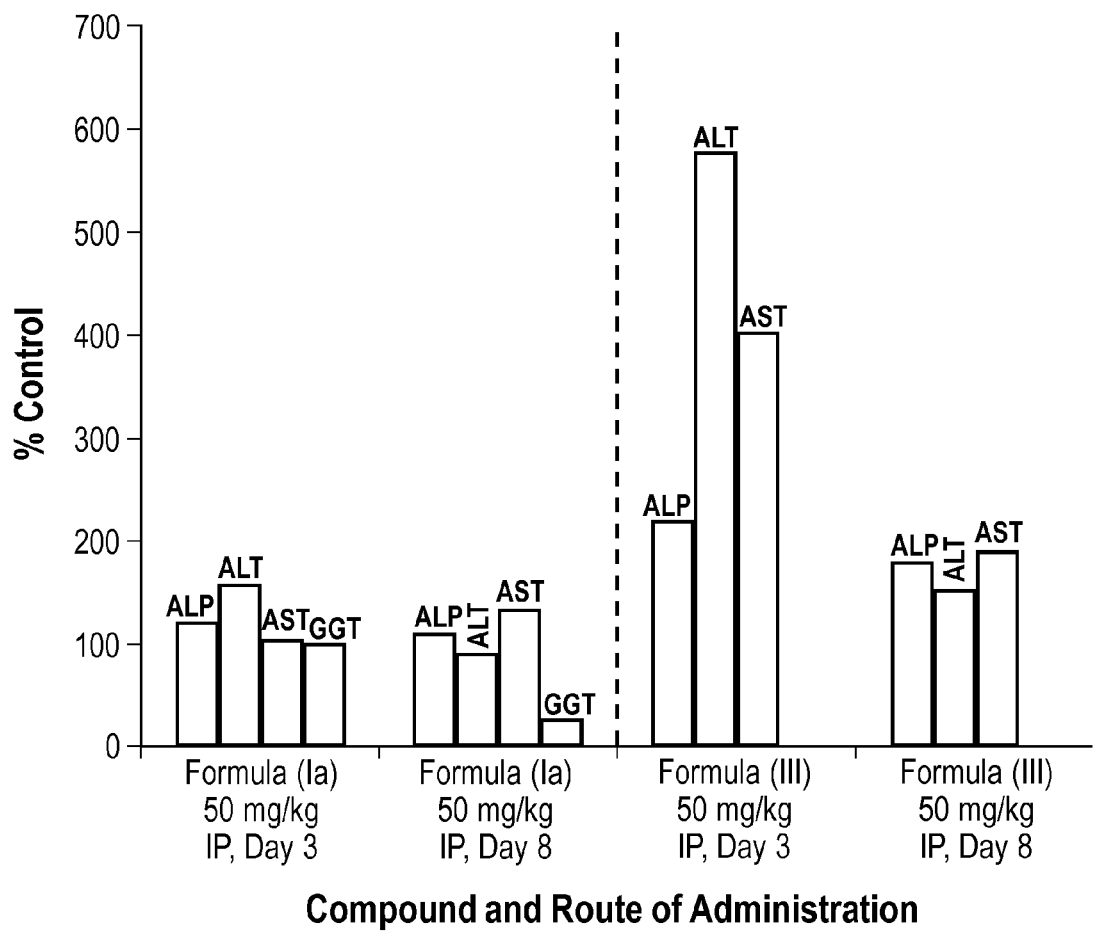
FIG. 6 is a bar graph of data showing the effect on hepatotoxicity biomarkers in rat serum for administering a compound of Formula (Ia) or a comparator compound of Formula (III) in a 7-day i.p. repeat dose screening toxicity study at 50 mg/kg/day for 7 consecutive days.

In contrast, the data in FIG. 6 for compounds of Formula (III) shows that the comparator compound of Formula (III) did elevate serum biomarkers of hepatotoxicity as compared to Formula (Ia) following the 7-day repeat dose of 50 mg/kg/day for 7 consecutive days.

Example 10

Pharmaceutical Composition Containing the Compound of Formula (Ia)

The components of a pharmaceutically acceptable formulation can include a compound of Formula (Ia) as the active ingredient, hydroxypropyl-β-cyclodextrin (HPBCD) as a solubilization and stabilization agent and HCl as the pH adjustor. The formulated dosing solution can comprise 10 mg/mL of the compound of Formula (Ia) and 25% (w/v) HPBCD dissolved in 0.1N hydrochloric acid (HCl), pH 2.0. The formulation can be converted to a lyophilized dosage form for reconstitution prior to dosing at the clinical site.

A drug product comprising the compound of Formula (Ia) can be a prepared by dissolving the compound of Formula (Ia) as the drug substance (DS) in 25% w/v HPBCD in a 0.1M HCl solution at a final target pH of 2 (±0.5). The compounded solution can be filled into vials for subsequent lyophilization.

Optionally, the pharmaceutical compositions comprising a compound of Formula (I) can be formed as nanosuspensions, co-crystals, spray dried dispersions and hot melt extrusions. These technologies can be selected based on their utilization and demonstrated success for BCS class II drug compounds. The feasibility assessment of the selected drug delivery technologies can be conducted using the HCl salt form of the compound of Formula (Ia) in Example 2.

The pharmaceutical composition can be a unit dose ranging from 200 to 500 mg in a size "00" capsule or equivalent tablet size. If 500 mg active/unit dose is achieved then development for that technology will be targeted to the highest achievable dose.

Preferably, the pharmaceutical compositions comprising the compound of Formula (Ia) can be formulated to provide a reduction in pain following surgery (e.g., management of pain following surgery compared to placebo to achieve about 50-100% reduction in opiate use within the first 24 hours after surgery). The pharmaceutical compositions comprising the compound of Formula (Ia) can be indicated for use for treatment of pain, including use as an orally administered analgesic and/or in compositions formulated for the treatment of pain caused by inflammation (e.g., to block acute pain and prevent or reduce inflammation at a wound site and prevent central sensitization). In one embodiment, the pharmaceutical compositions comprising the compound of Formula (Ia) can be administered BID for a suitable time period (e.g., 7-14 days) and provide analgesia within about 30 minutes of administration. Preferably, the pharmaceutical composition(s) comprising the compound of Formula (Ia) can provide clinically measureable decreases in pain scores, without respiratory depression and/or drug-induced CNS effects.

Example 11

Single Ascending Dose Phase 1A Study

A randomized, double-blind, placebo-controlled, crossover, single dose, safety, tolerability and pharmacokinetic study of 6 ascending doses of the compound of Formula (Ia) was undertaken in two cohorts of healthy male volunteers. A total of eighteen eligible healthy mail volunteers were recruited utilizing an alternating panel design. The first cohort of nine subjects (Cohort 1) was sequentially enrolled into 3 of 6 dosing periods (Dose Levels 1, 3, and 5). The remaining cohort of nine subjects (Cohort 2) was enrolled in the other 3 dosing periods (Dose Levels 2, 4, and 6). Within each dosing period, subjects were randomly assigned 2:1 to the compound of Formula (I) (n=6) or placebo (n=3). Each subject received one dose of placebo and two different doses of the compound of Formula (I) over the course of their participation in all three dosing periods. Subjects were equally randomized to one of 3 possible sequences, namely 1) placebo, active, active, 2) active, placebo, active, and 3) active, active, placebo.

The single ascending dose Phase 1A study was successfully completed with no safety signals seen that were attributable to the compound of Formula (Ia).

INCORPORATION BY REFERENCE

All publications and patents mentioned herein are hereby incorporated by reference in their entirety as if each individual publication or patent was specifically and individually indicated to be incorporated by reference.

EQUIVALENTS

Those skilled in the art will recognize, or be able to ascertain using no more than routine experimentation, many equivalents to the specific embodiments of the invention described herein. Such equivalents are intended to be encompassed by the following claims.

We claim:

1. A method for treating or ameliorating pain, comprising intravenously administering to an animal or human an effective amount of a pharmaceutical composition comprising a compound of Formula (Ia), or a pharmaceutically acceptable salt thereof:

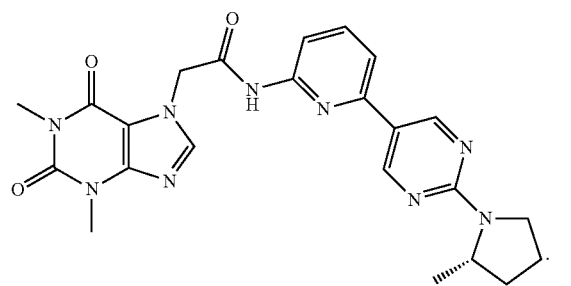

(Ia)

2. The method of claim 1, wherein the compound of Formula (Ia) is in the form of a hydrochloride salt.

3. The method of claim 1, wherein the pain is acute pain.

4. The method of claim 1, wherein the pain is chronic pain.

5. The method of claim 1, wherein the pain is post-surgical pain.

6. The method of claim 1, wherein the pain is inflammatory pain.

7. A compound of Formula (Ia), or a pharmaceutically acceptable salt of the compound of Formula (Ia):

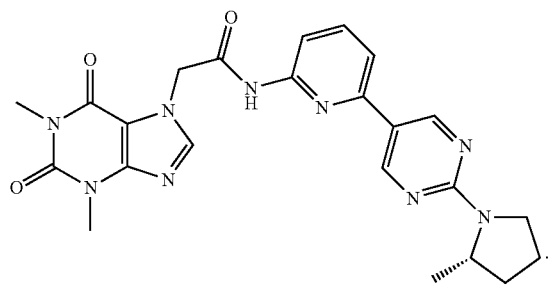
(Ia)

8. The compound of claim 7, comprising the hydrochloride salt of the compound of Formula (Ia).

9. A compound of Formula (I), or a pharmaceutically acceptable salt thereof:

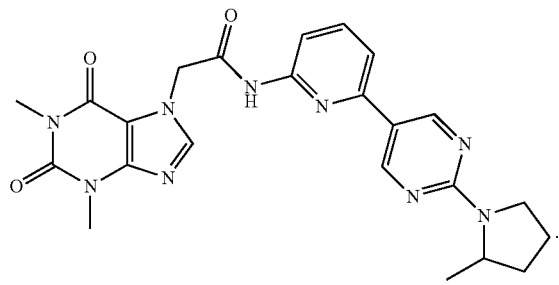
(I)

10. A compound according to claim 9 in the form of its hydrochloride salt.

11. A method for treating or ameliorating pain, comprising orally administering to an animal or human an effective amount of a pharmaceutical composition comprising a compound of Formula (Ia), or a pharmaceutically acceptable salt thereof:

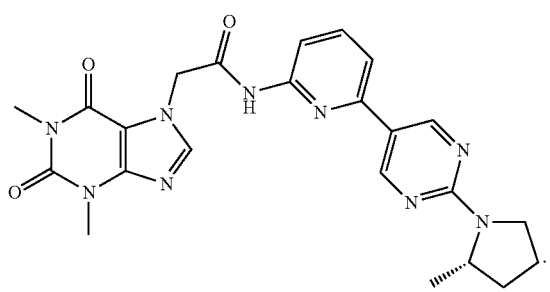
(Ia)

* * * * *